US012636455B2

(12) United States Patent
Lin et al.

(10) Patent No.: US 12,636,455 B2
(45) Date of Patent: May 26, 2026

(54) PATIENT INTERFACE

(71) Applicant: Wellell Inc., New Taipei City (TW)

(72) Inventors: Shin-Lan Lin, New Taipei City (TW);
Yi-Ting Tseng, New Taipei City (TW);
Shu-Chi Lin, New Taipei City (TW);
Chih-Tsan Chien, New Taipei City
(TW)

(73) Assignee: WELLELL INC., New Taipei City
(TW)

( * ) Notice: Subject to any disclaimer, the term of this
patent is extended or adjusted under 35
U.S.C. 154(b) by 887 days.

(21) Appl. No.: 17/667,579

(22) Filed: Feb. 9, 2022

(65) Prior Publication Data

US 2022/0273899 A1 Sep. 1, 2022

(30) Foreign Application Priority Data

Feb. 26, 2021 (TW) .................................. 110107046

(51) Int. Cl.
*A61M 16/06* (2006.01)
*A61M 16/08* (2006.01)
(52) U.S. Cl.
CPC .... *A61M 16/0611* (2014.02); *A61M 16/0683*
(2013.01); *A61M 16/0816* (2013.01)
(58) Field of Classification Search
CPC .............. A61M 16/06; A61M 16/0605; A61M
16/0611; A61M 16/0616; A61M 16/0622;
A61M 16/0627; A61M 16/0633; A61M
16/0638; A61M 16/0644; A61M 16/065;

A61M 16/0655; A61M 2016/0661; A61M
16/0875; A61M 16/0816; A61M 16/08;
A61M 16/0683; A61M 2205/42;
(Continued)

(56) References Cited

U.S. PATENT DOCUMENTS 8,550,084 B2 * 10/2013 Ng .................... A61M 16/0694
128/206.28
2006/0081248 A1 * 4/2006 McDonald ............ A61M 16/06
128/205.25
(Continued)

FOREIGN PATENT DOCUMENTS

NZ 585826 A * 11/2011
WO WO-2004022146 A1 * 3/2004 ............ A61M 16/06
(Continued)

*Primary Examiner* — Timothy A Stanis
*Assistant Examiner* — Thomas Z Chang
(74) *Attorney, Agent, or Firm* — WPAT, PC

(57) ABSTRACT

The present invention provides a patient interface including
a cushion assembly, a headgear assembly, an elbow assem-
bly and transition ring structure and a headgear secure
assembly. The cushion assembly, the elbow assembly and
the headgear secure assembly are assembled together by the
transition ring structure. The cushion assembly is sealed
with a face of a patient when in use. The headgear secure
assembly is for connecting the headgear so as to secure the
patient interface at the face of the patient when in use. The
cushion assembly is provided with a cylindrical wall for
delivering an air flow, and the cylindrical wall projects in
two opposite directions along an axis of an opening thereof,
so as to provide an air flow of a breathing chamber with a
flow diversion guiding effect. Thus, the patient interface can
be worn and used with better comfort and convenience.

16 Claims, 29 Drawing Sheets

(58) Field of Classification Search

CPC .. B29C 66/11; B29C 66/2442; F16L 27/0861;
F16L 27/0804; F16L 27/00; F16L 33/00;
A62B 9/04; A62B 18/006; A62B 18/00;
A62B 18/02; A62B 18/06; A62B 18/084

See application file for complete search history.

(56) References Cited

U.S. PATENT DOCUMENTS

| | | | | |
|---|---|---|---|---|
| 2006/0201514 A1* | 9/2006 | Jones | ................ | A61M 16/0683 |
| | | | | 128/206.24 |
| 2009/0194111 A1* | 8/2009 | Fu | ......................... | A61M 16/08 |
| | | | | 128/205.24 |
| 2014/0150798 A1* | 6/2014 | Fong | ................ | A61M 16/0825 |
| | | | | 128/206.21 |
| 2015/0144140 A1* | 5/2015 | Eury | ..................... | A61M 16/06 |
| | | | | 128/206.24 |

FOREIGN PATENT DOCUMENTS

| | | | | | |
|---|---|---|---|---|---|
| WO | WO-2011060479 A1 * | 5/2011 | ............ | A61M 16/06 |
| WO | WO-2017049356 A1 * | 3/2017 | ........ | A61M 16/0057 |

* cited by examiner

140

143

140

144        142

141

141   143

144

142

1421     A-A

145

B-B

C-C

510'

514

516

511

512

515

513

518

517

PATIENT INTERFACE

BACKGROUND OF THE INVENTION

Field of the Invention

The present invention relates to a patient interface, and more particularly, to a patient interface used for a continuous positive airway pressure (CPAP) respirator.

Description of the Prior Art

A continuous positive airway pressure (CPAP) respirator is equipment used for treating obstructive sleep apnea (OSA). By covering a nose of a patient or covering both a mount and a nose of a patient using a patient interface, air or other breathable gas is continuously supplied to the patient, and a continuous positive pressure is maintained to open up congested airways of the patient and keep the airways unobstructed, further achieving an object treating OSA.

When the equipment is in use, an air flow is generated from air for breathing by a flow generator, and the air for breathing is delivered through a delivery tube to the patient interface and then provided to the patient. Air exhaled by the patient is also discharged through the patient interface. The patient interface accommodates the air flow generated by the flow generator and the air flow exhaled by the patient, and at the same time an air discharge function needs to be provided for the air flow exhaled by the patient. As a result, air flow disturbances are likely to occur in the patient interface, and may thus easily cause noise and lead to discharge difficulties of carbon dioxide in the gas exhaled by the patient.

SUMMARY OF THE INVENTION

It is an object of the present invention to provide a patient interface that can be worn and used with comfort and convenience for a patient using a continuous positive airway pressure (CPAP) respirator or a user using other supply device supplying breathing air.

It is another object to reduce a noise level produced by an air flow when a patient wears a patient interface and uses a CPAP respirator, further enhancing comfort of use.

To achieve the above and other objects, the present invention provides a patient interface that delivers an air flow within a treatment pressure range of 2 to 30 cm H2O generated by an air flow generator to airways of a patient at a continuous positive pressure relative to the ambient air pressure. The patient interface includes a cushion assembly, a headgear assembly, a frame assembly and an elbow assembly. The cushion assembly includes a shield, a cylindrical wall and a soft sealing member. The shield has an opening structured on a first end of the cushion assembly, and a ring structure projecting from the opening in a direction towards the first end of the cushion assembly. The cylindrical wall is provided to the opening by a plurality of support structures and formed as concentric with the opening, and projects in two opposite directions along an axis of the opening. The soft sealing member is provided to the shield of the cushion assembly and together form a breathing chamber, and is adapted to airtightly press against at least portion of a face of a patient. The frame assembly is adapted to engage with the cushion assembly, includes a plurality of slots adapted to attach to respective ones of the straps in use, and is not provided with a forehead support. The elbow assembly is adapted to be connected to an air delivery tube connected to a flow generator so as to deliver an air flow to airways of the patient when in use, and is non-detachably provided to the frame assembly. When attached, the frame assembly and the cushion assembly are rotatable in between.

According to an embodiment of the present invention, a cushion assembly includes a hollow structure, a cylindrical wall and a sealing assembly. The hollow structure has a central aperture structured on a first end of the cushion assembly to deliver an air flow when in use, and a protruding structure projecting from the central aperture in a direction towards the first end of the cushion assembly. The cylindrical wall is provided to the central aperture, and is structured to be substantially concentric with the central aperture. The cylindrical wall projects in the manner of having a same diameter towards the first end of the cushion assembly by a first distance, and projects in a manner of having a different diameter towards the second end opposite to the first end of the cushion assembly by a second distance, wherein the first distance is greater than the second distance. The sealing assembly is provided to the hollow structure of the cushion assembly and together formed a breathing chamber, and is adapted to seal a face of a patient in response to wearing of the patient to prevent the hollow structure from contacting the face of the patient.

According to an embodiment of the present invention, a frame assembly includes a transition ring structure and a headgear secure assembly. The transition ring structure is provided to the cushion assembly by means of a rigid-to-rigid connection, and has one end for arranging the elbow assembly and allowing 360-degree rotation of the elbow assembly. The headgear secure assembly is adapted to engage with the transition ring structure, and has a central opening for accommodating the elbow assembly. The headgear secure assembly includes a pair of headgear clip attachment portions adapted to engaged with the corresponding pair of headgear clips so as to attach to the corresponding lower straps, and a pair of upper openings adapted to attach to the corresponding upper straps to secure the headgear assembly to the head of the patient when in use. Moreover, the headgear secure assembly is not provided with a forehead support.

According to an embodiment of the present invention, a cushion assembly includes a hollow structure and a cylindrical wall. A seal forming assembly further included is structured to form sealing with a nose and/or a mouth of a patient. The seal forming assembly and the hollow structure together form an inflating chamber that applies a pressure to a treatment pressure, and a first support area and a second support area of the seal forming assembly together prevent the hollow structure from contacting a face of the patient. The thickness of the first support area is substantially greater than the thickness of the second support area, and the thickness of the first support area gradually decreases towards the second support area. A border is formed between the first support area and the second support area on the seal forming assembly, and the thickness of the seal forming assembly on the border is substantially constant.

According to an embodiment of the present invention, the headgear assembly includes a plurality of upper straps, a plurality of lower straps, and a rear strap assembly. The upper straps are configured to extend to above ears of a patient when in use. The lower straps are configured to extend to below ears of a patient when in use. The rear strap assembly is provided to the upper straps and the lower straps. The rear strap assembly includes a top portion, a plurality of side portions and a bottom portion. The top portion is provided between the side portions, the bottom portion is provided between the side portions and the lower straps, and the upper straps are provided to the corresponding side portions. A first strap distance between an intersection of each side portion and the top portion may be smaller than a second strap distance between an intersection of each side portion and the bottom portion, and the first strap distance may be greater than a third strap distance between the intersection of each side portion and each upper strap.

According to an embodiment of the present invention, the elbow assembly is provided to the transition ring structure and is 360-degree rotatable, and includes a first end, a second end and a body. The first end has a bent outer structure. The second end is adapted to connect to an air delivery tube of the flow generator so as to deliver an air flow to airways of a patient when in use. The bent outer structure of the first end and at least a portion of the transition ring structure together form in a non-releasable manner an air pathway when in use. Most of an incoming air flow delivered from the flow generator to the breathing chamber passes through the conduit air pathway and an inner surface of the cylindrical wall of the cushion assembly, most of an outgoing air flow discharged from the breathing chamber to an ambient environment passes through a space between an outer surface of the cylindrical wall of the cushion assembly and an inner surface of the protruding structure, and the bent outer structure of the first end at least a portion of the transition ring structure are used to form the air pathway when in use.

According to an embodiment of the present invention, the transition ring structure (or referred to as a connecting ring structure) and the cushion assembly can be structured to attach with each other in a non-resist movement manner between the two.

According to an embodiment of the present invention, the hollow structure (or referred to as a shield) and the sealing assembly (or referred to as a seal forming assembly or a soft sealing member) may be integral-molded.

According to an embodiment of the present invention, any part of the seal forming assembly (or referred to as a soft sealing member or a sealing assembly) may exclude a double-layer structure.

According to an embodiment of the present invention, the cushion assembly, the elbow assembly and the headgear secure assembly may exclude direct physical contact/engagement in between.

Accordingly, the embodiments achieve multiplied effects, and the patient interface can be stably secured on the face of a patient with comfort and effectively reduce a noise level.

DETAILED DESCRIPTION OF THE EMBODIMENTS

Objectives, features, and advantages of the present disclosure are hereunder illustrated with specific embodiments, depicted with drawings, and described below.

In the disclosure, descriptive terms such as "a" or "one" are used to describe the unit, component, structure, device, module, system, portion or region, and are for illustration purposes and providing generic meaning to the scope of the present invention. Therefore, unless otherwise explicitly specified, such description should be understood as including one or at least one, and a singular number also includes a plural number.

In the disclosure, descriptive terms such as "include, comprise, have" or other similar terms are not for merely limiting the essential elements listed in the disclosure, but can include other elements that are not explicitly listed and are however usually inherent in the units, components, structures, devices, module, systems, portions or regions.

In the disclosure, the terms similar to ordinals such as "first" or "second" described are for distinguishing or referring to associated identical or similar components or structures, and do not necessarily imply the orders of these components, structures, portions or regions in a spatial aspect. It should be understood that, in some situations or configurations, the ordinal terms could be interchangeably used without affecting the implementation of the present invention.

A patient interface disclosed in the embodiments below relates to delivery of an air flow generated by a flow generator to airways of a patient (or other individual wearing the patient interface) to further construct a treatment system. A flow generator can apply a treatment pressure to a part such as airways of a patient or an entrance of airways of a patient, wherein the entrance of the airway of a patient includes at least, for example, an entrance of a nose cavity and/or an entrance of a mouth cavity of a patient. The treatment pressure is defined as a continuous positive pressure relative to an atmosphere where a patient is located, and is, for example, a continuous positive pressure between a pressure range of 2 cm H2O to 30 cm H2O. The treatment pressure is capable of improving a situation of breathing disorders caused by such as sleep breathing disorders of a patient.

1. The Patient Interface and an Overall of the Treatment System

Figure 1:
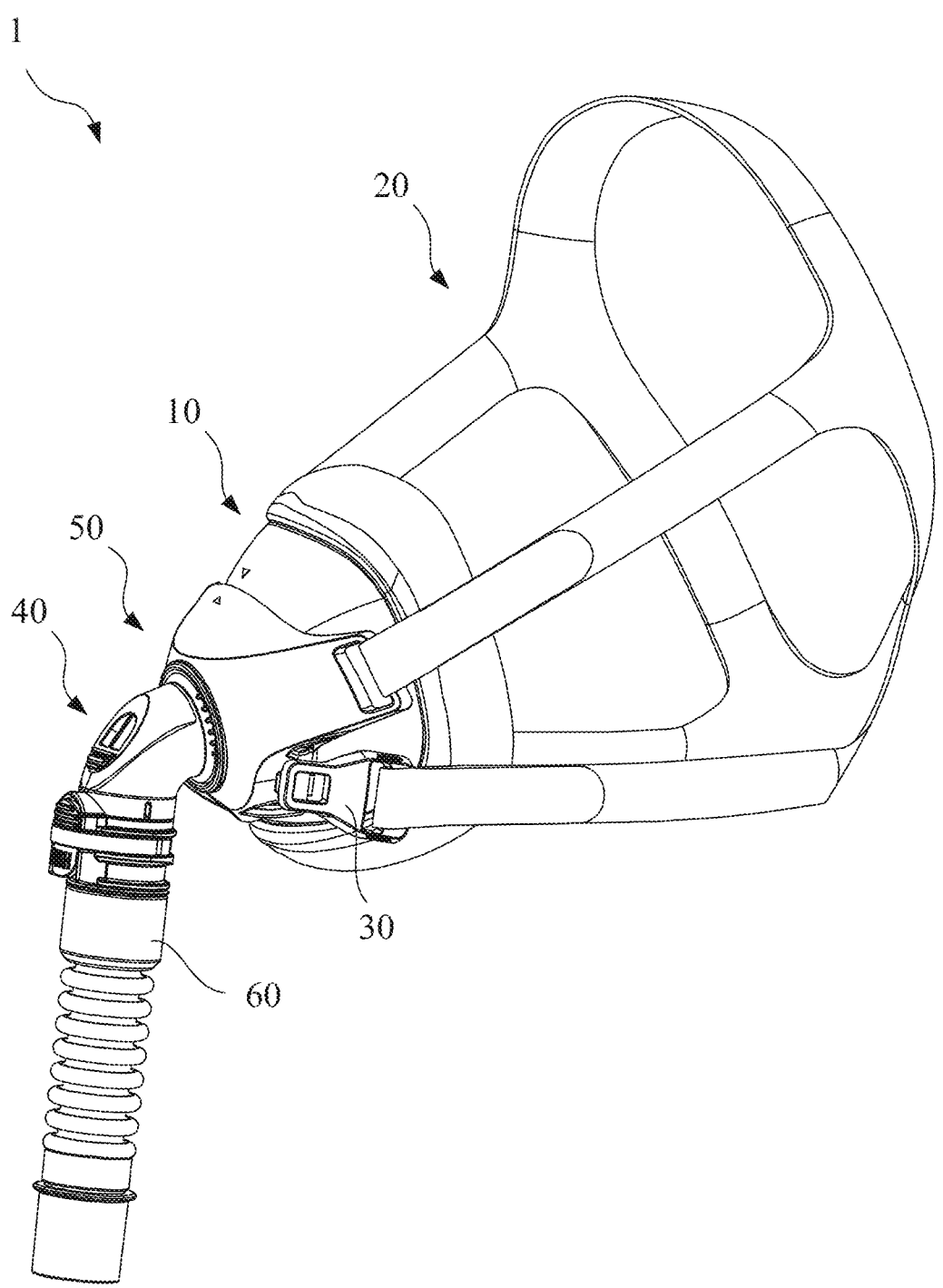
FIG. 1 is a three-dimensional schematic diagram of a patient interface according to an embodiment of the present invention.
Figure 2:
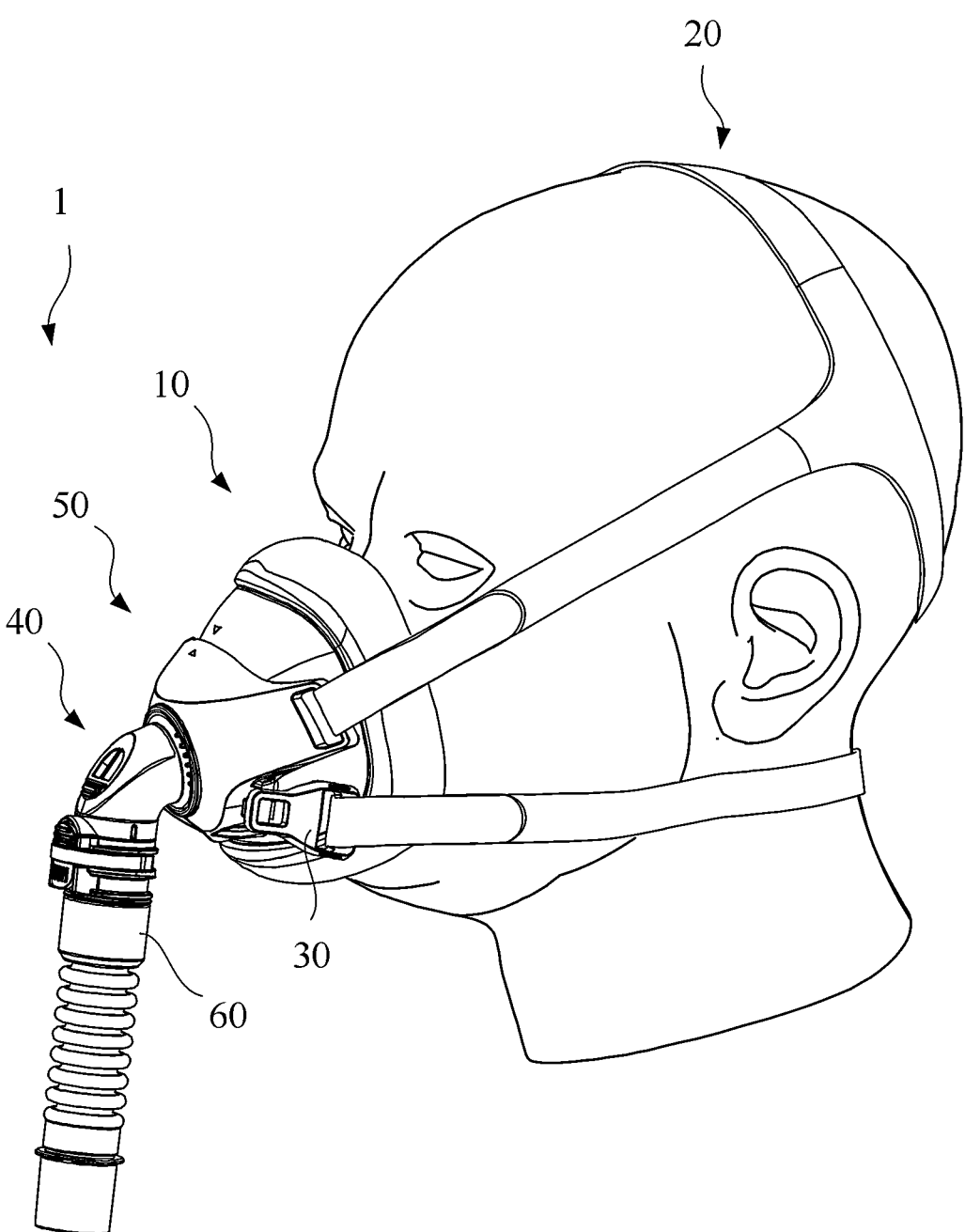
FIG. 2 is a three-dimensional schematic diagram of a patient interface worn at a head of a patient according to an embodiment of the present invention.

Referring to FIG. 1 and FIG. 2, FIG. 1 shows a three-dimensional schematic diagram of a patient interface according to an embodiment of the present invention, and FIG. 2 shows a three-dimensional schematic diagram of a patient interface worn at a head of a patient according to an embodiment of the present invention. As shown in FIG. 2, the patient interface in the treatment system serves as an interface secured at a head of a patient, and is for delivering an air flow generated by a flow generator to airways of the patient or an entrance of airways of the patient.

In aspect of wearing stability and comfort of the patient, the present patient interface is designed such that, even without a forehead support, the patient interface can be stably secured at an appropriate position of the head of the patient with coordination of various parts, and a smooth flow field is formed between the air flow delivered to the patient and an air flow exhaled by the patient, allowing the patient under treatment or the wearer to receive positive-pressure treatment in a stable and comfortable treatment environment.

As shown in FIG. 1 and FIG. 2, the patient interface 1 according to this embodiment includes a cushion assembly 10, a headgear assembly 20, headgear clips 30, an elbow assembly 40 and a frame assembly 50. Together with the fine adjustment of the headgear assembly, the frame assembly 50 with the cushion assembly 10 engaging one end of the frame assembly 50, the patient interface 1 is stably secured on an appropriate position of the face of the patient. A breathing chamber may be defined between the cushion assembly 10 and the face of the patient. The breathing chamber receives and inputs the positive-pressure air flow sent from the elbow assembly 40 to airways of the patient, and at the same time, the elbow assembly 40 also receives and outputs an air flow exhaled by the patient to the ambient environment.

The other end of the frame assembly 50 may be used for arranging the elbow assembly 40, such that the air flow delivered from the flow generator (not shown) through an air delivery tube 60 is guided by the elbow assembly 40 and flows into the breathing chamber through the frame assembly 50. The frame assembly 50 enables the headgear assembly 20 to be placed around a predetermined part of a head of the patient through an attachment position of the frame assembly 50 and the headgear assembly 20 are directly and/or indirectly attached therewith, and the attachment is also designed to avoid covering regions where may cause uncomfortable situation to the patient (for example, ears). In the embodiments shown in FIG. 1 and FIG. 2, an indirect attachment may be formed by the headgear clips 30 between the frame assembly 50 and a portion of the headgear assembly 20.

2. The Structures of a Headgear Secure Assembly/Frame Assembly

Figure 3:
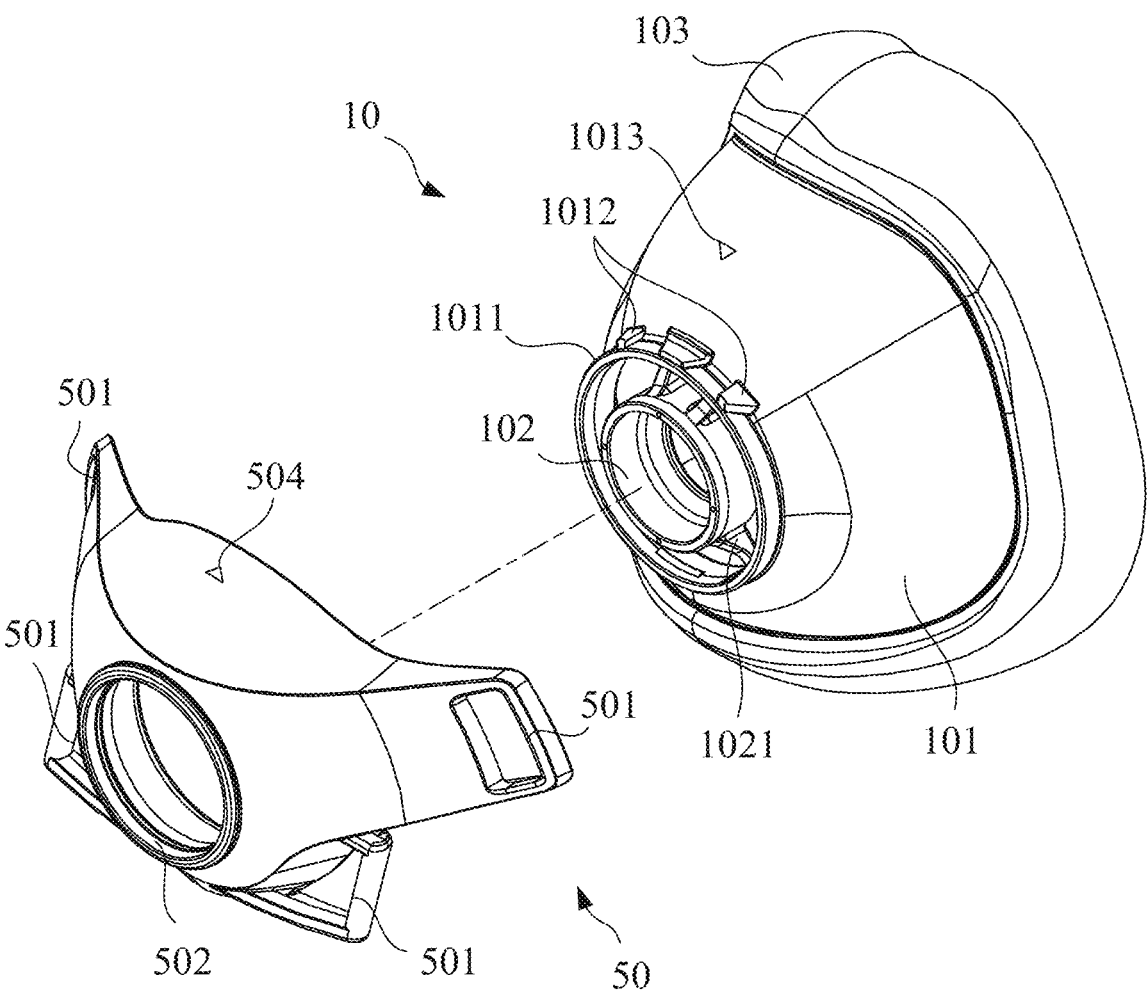
FIG. 3 is a three-dimensional schematic diagram of a frame assembly engaged with a cushion assembly according to an embodiment of the present invention.
Figure 4:
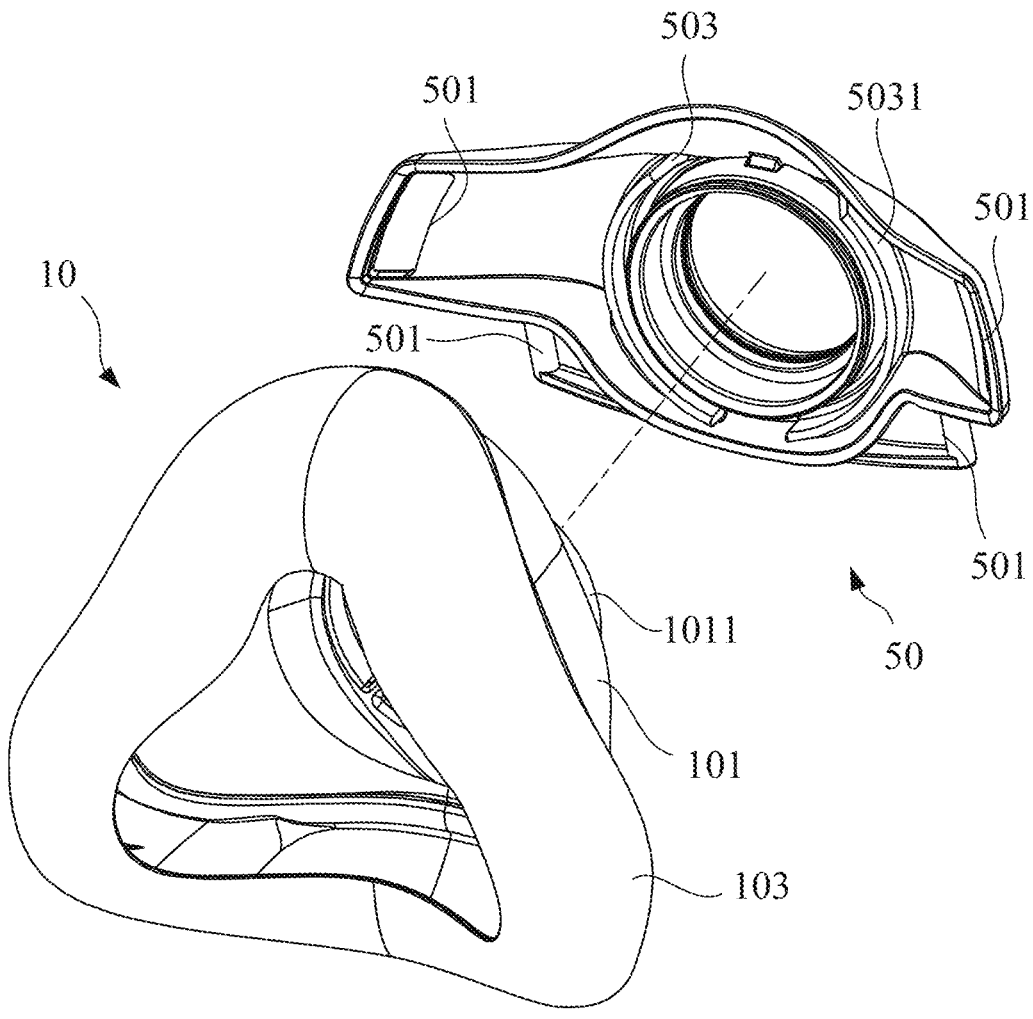
FIG. 4 is a three-dimensional schematic diagram of a frame assembly in FIG. 3 from another perspective.

Referring to FIG. 3 and FIG. 4, FIG. 3 shows a three-dimensional schematic diagram of a frame assembly engaged with a cushion assembly according to an embodiment of the present invention, and FIG. 4 shows a three-dimensional schematic diagram of the frame assembly in FIG. 3 from another perspective. The frame assembly 50 includes a plurality of slots 501 on two opposite side edges thereof. The slots 501 may be used for direct and/or indirectly attachment to the headgear assembly 20. The examples in FIG. 1 and FIG. 2 include attachment of two modes (direct and indirect), two slots 501 on an upper portion of the frame assembly 50 are for direct attachment to corresponding straps in the headgear assembly 20, and two slots 501 on a lower portion of the frame assembly 50 are for indirect attachment to corresponding straps in the headgear assembly 20 through an additional pair of headgear clips 30. The indirect attachment of the lower portion of the frame assembly 50 can further provide the patient or the wearer with enhanced comfort and convenience during putting on and taking off. For example, the headgear clips 30 can be operated to be attached to the slots 501 or removed from the slots 501 with enhanced convenience. The replaceable headgear clips 30 also provides degree of freedom of rotation, providing the headgear assembly 20 with options of different attachment angles when attached to the frame assembly 50.

As shown in FIG. 3 and FIG. 4, the cushion assembly 10 includes a shield 101, a cylindrical wall 102 and a sealing assembly 103. The shield 101 has an opening structured on a first end of the cushion assembly 10, and a ring structure 1011 projecting from an edge of the opening in a direction towards the first end of the cushion assembly 10. The cylindrical wall 102 is provided to the opening by a plurality of support structures 1021 and is concentric with the opening. Compared to the shield 101, the sealing assembly 103 is a softer assembly, or may be referred to as a soft sealing member. The sealing assembly 103 is provided to the shield 101. A breathing chamber is formed by a space between the sealing assembly 103 coordinating with the shield 101 and the face of the patient. The sealing assembly 103 is adapted to airtightly press against at least portion of the face of the patient. The shield 101 and the sealing assembly 103 may be integral-molded.

Further, the ring structure 1011 of the cushion assembly 10 is provided with a rotation limiting block 1012 at an upper edge, and the frame assembly 50 is provided with a rotation limiting notch 503 at the opening 502. The rotation limiting notch 503 is, for example, a notch formed on a limiting wall 5031, so as to achieve a limiting function. The rotation limiting block 1012 may be blocked by the rotation limiting notch 503, so the relative rotation between the cushion assembly 10 and the frame assembly 50 can be achieved but limited (not 360 degree free rotation). The limiting wall 5031 is structured on one end of the frame assembly 50 facing the cushion assembly 10, and the limiting wall 5031 is a wall structure projecting in a direction towards the cushion assembly 10.

Further, the shield 101 may be provided with an alignment guide 1013, and the frame assembly 50 is provided correspondingly with an alignment indicator 504, so as to provide a user with guidance for mounting the cushion assembly 10 on the frame assembly 50. Meanwhile, on the basis of the coordination of the alignment guide 1013 and the alignment indicator 504, an extent of relative displacement between the cushion assembly 10 and the frame assembly 50 after the mounting may also be an indication for the user or the patient.

Figure 5:
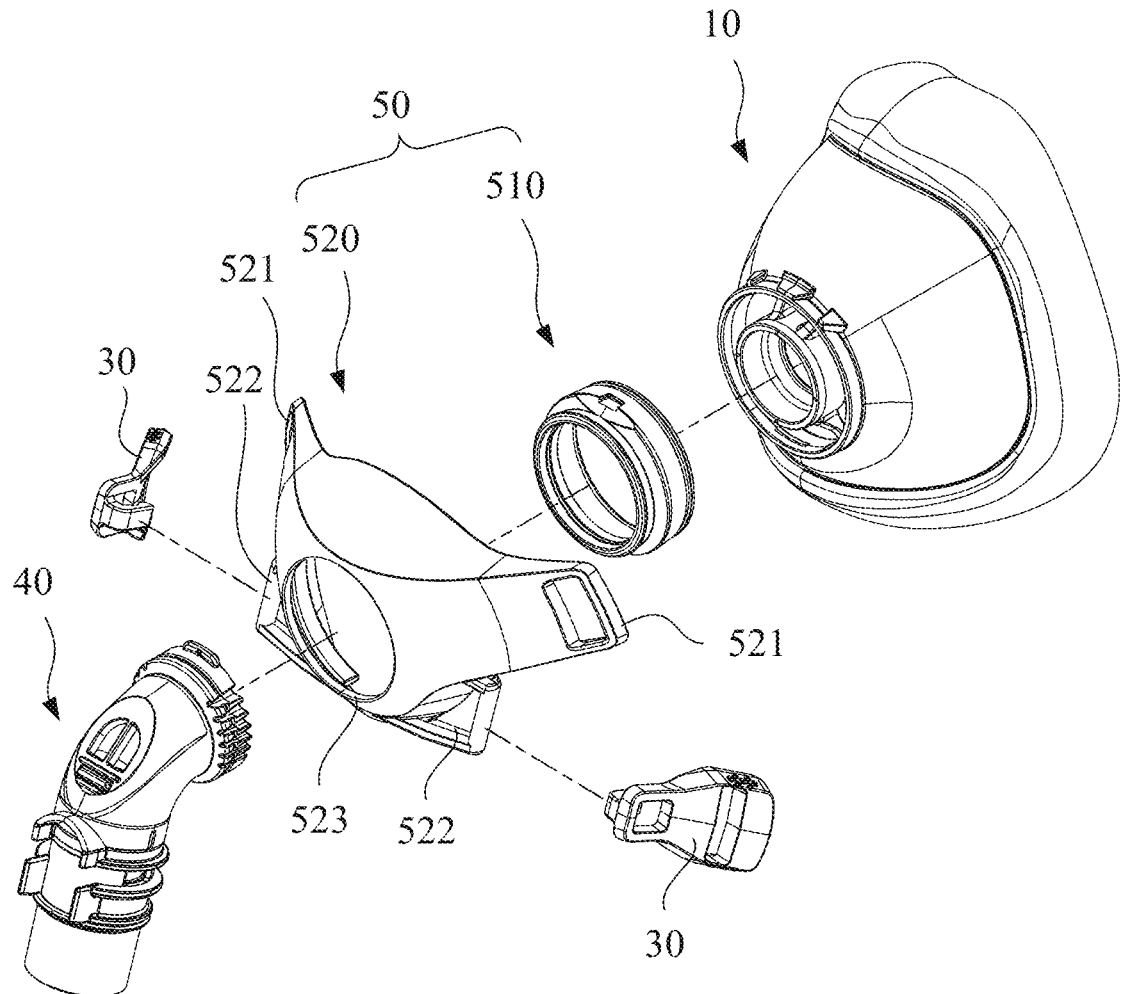
FIG. 5 is a three-dimensional schematic diagram of a frame assembly engaged with a cushion assembly according to another embodiment of the present invention.

FIG. 5 shows a three-dimensional schematic diagram of a frame assembly according to another embodiment of the present invention. The frame assembly 50 includes a transition ring structure 510 and a headgear secure assembly 520. The transition ring structure 510 has one end used for engaging with the cushion assembly 10, and the other end used for engaging with the headgear secure assembly 520. In one implementation aspect of the embodiment, the headgear secure assembly 520 and the cushion assembly 10 may be engaged with outer surfaces of two end edges of the transition ring structure 510, so that the headgear secure assembly 520 and the cushion assembly 10 may exclude direct physical contact/engagement in between. In this embodiment, the transition ring structure 510 serves as a connection medium between the headgear secure assembly 520 and the cushion assembly 10, and may also be regarded as a connecting ring structure.

As shown in FIG. 5, the headgear secure assembly 520 includes a pair of upper openings 521, a pair of headgear attachment portions 522 and a central opening 523. The central opening 523 is for accommodating the elbow assembly 40, the pair of headgear clip attachment portions 522 are for attaching the corresponding headgear clips 30, and the pair of upper openings 521 are for attaching the corresponding straps of the headgear assembly 20. In this embodiment, the elbow assembly 40 is secured in the central opening 523 by means of being engaged with an inner surface of the transition ring structure 510. The elbow assembly 40 may be provided to the transition ring structure 510 further by a non-detachable manner.

Further, in one implementation aspect of the embodiment, the headgear secure assembly 520 and the cushion assembly 10 are engaged on the outer surfaces at two end edges of the transition ring structure 510, and the elbow assembly 40 is engaged on the inner surface of the transition ring structure 510. Thus, the cushion assembly 10, the elbow assembly 40 and the headgear secure assembly 520 are not in direct physical contact/engagement in a state of use after the engagement.

3. The Structure of the Cushion Assembly

Figure 6:
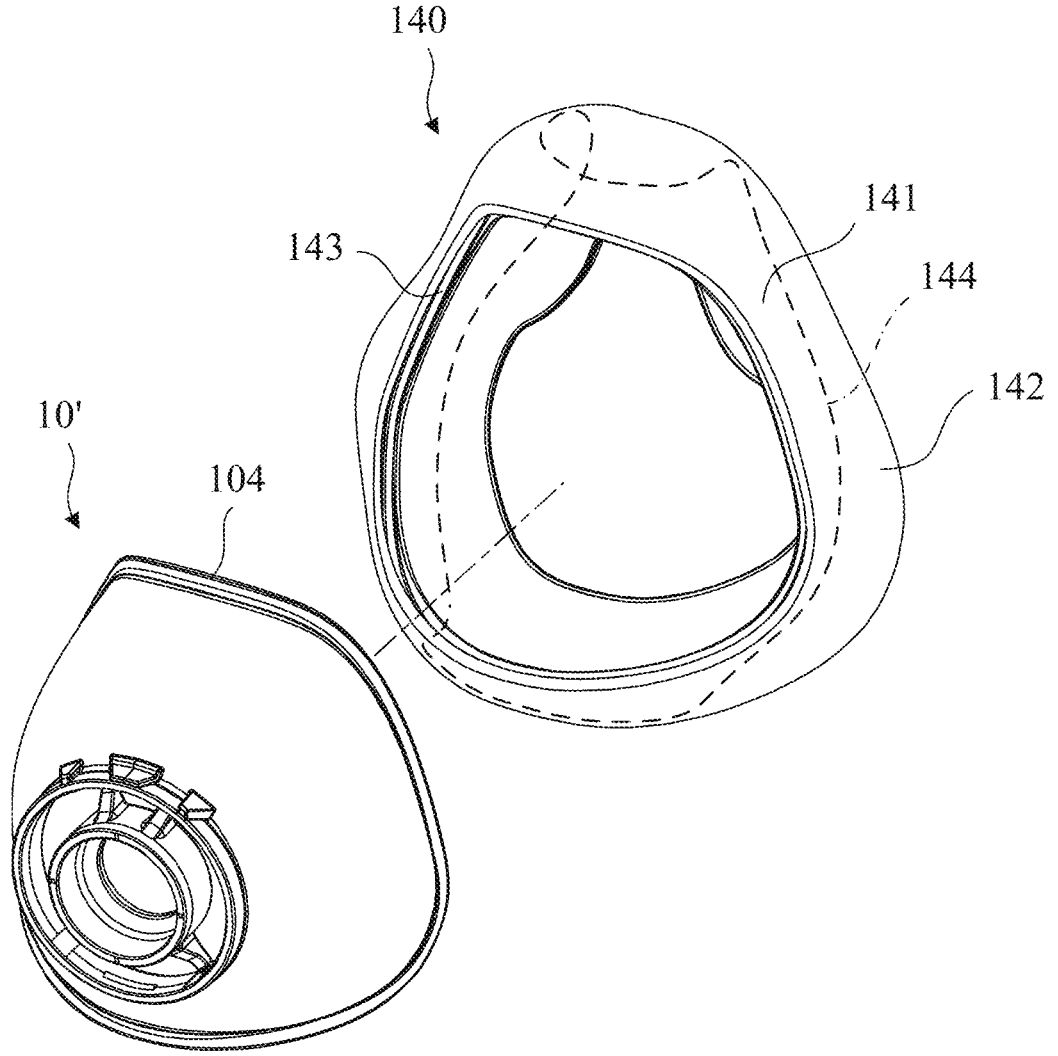
FIG. 6 is a three-dimensional schematic diagram of a cushion assembly arranged on a seal forming assembly according to an embodiment of the present invention.

FIG. 6 shows a three-dimensional schematic diagram of a cushion assembly arranged on a seal forming assembly according to an embodiment of the present invention. Via an engaging portion 143 of the seal forming assembly 140, a cushion assembly 10' and the seal forming assembly 140 are engaged. The engagement may be implemented by means of injection molding or overmolding. The seal forming assembly 140 is adapted to seal the face of a patient in use, and accordingly, the cushion assembly 10' and the seal forming assembly 140 together form an inflating chamber that can be applied a pressure to a treatment pressure due to the sealing of the patient's face.

As shown in FIG. 6, the seal forming assembly 140 includes a first support area 141 and a second support area 142. The first support area 141 is provided on an end portion 104 of a second end of the cushion assembly 10'. The end portion 104 is an engaging portion for engaging (for example, by injection molding or overmolding) to the first support area 141. The second support area 142 is provided at the first support area 141, and allows a support area to extend to different extents. Between the first support area 141 and the second support area 142 is a border 144, and the border 144 is formed based on a degree of change in the thickness of the two support areas. In another embodiment, a vicinity between the first support area 141 and the end portion 104 may also be referred to as a first border, and a vicinity between the first support area 141 and the second support area 142 may be referred to as a second border.

In response to improving wearing comfort for a patient, the seal forming assembly 140 does not include any part that is a double-layer structure, and the second support area 142 at least contacts a nose bridge and/or a chin area of the patient. Taking the embodiment in FIG. 6 for instance, the first support area 141 and the second support area 142 may be together used for preventing a specific portion of the cushion assembly 10 from contacting the face of the patient. The specific portion refers to a portion of the end portion 104 of the cushion assembly 10' that extends in a direction towards a first end opposite to the second end.

In this embodiment, in one implementation aspect, the thickness of the first support area 141 is substantially greater than the thickness of the second support area 142, and the thickness of the first support area 141 gradually decreases in a direction towards the second support area 142. Moreover, the thickness of the border 144 formed between different support areas on the seal forming assembly 140 may be substantially constant.

Figure 7:
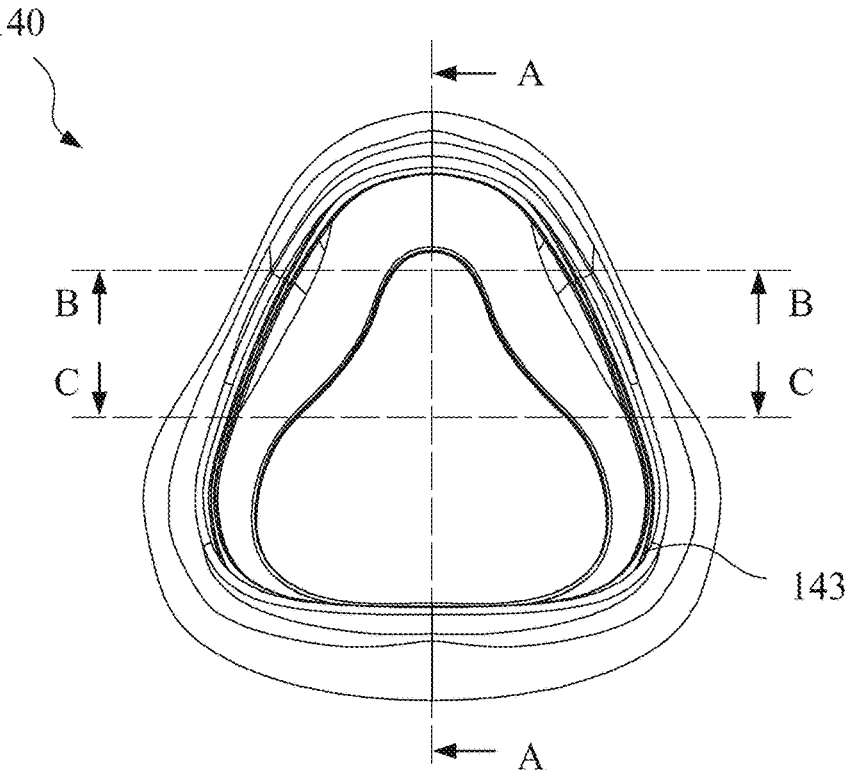
FIG. 7 is a front view of a seal forming assembly according to an embodiment of the present invention.
Figure 8:
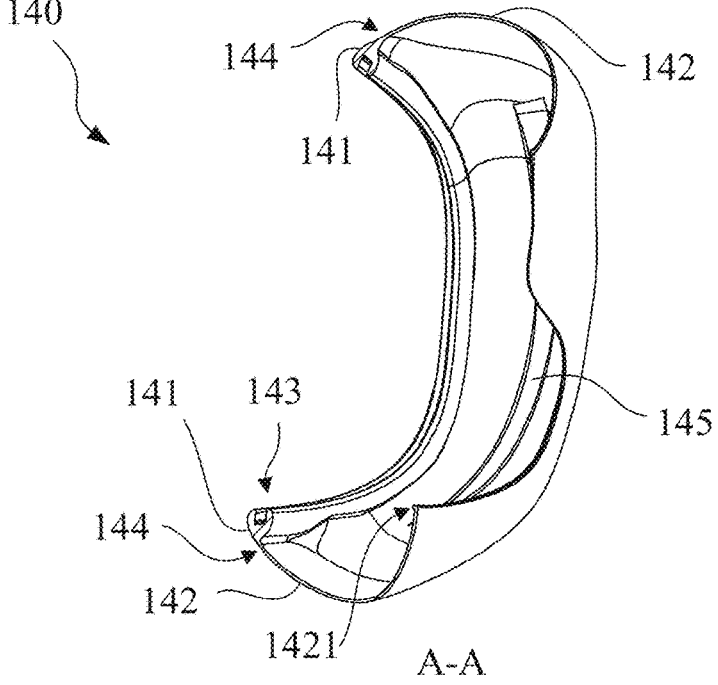
FIG. 8 is a section schematic diagram along section line AA in FIG. 7.
Figure 9:
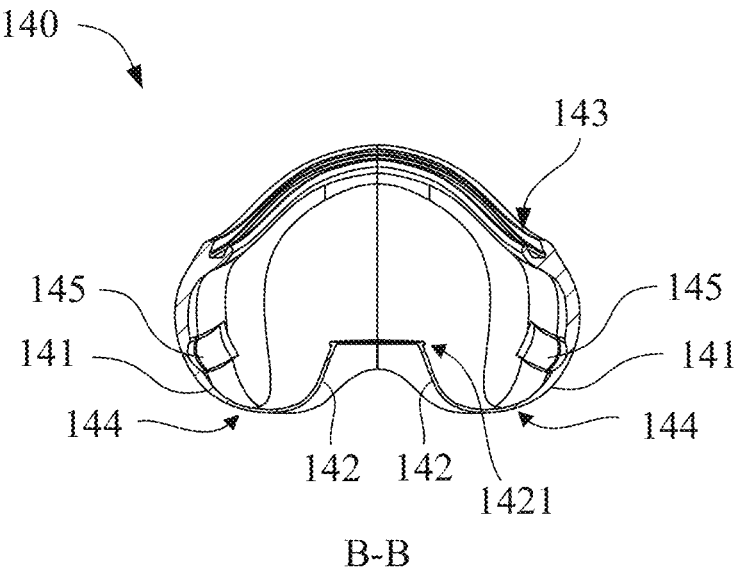
FIG. 9 is a section schematic diagram along section line BB in FIG. 7.
Figure 10:
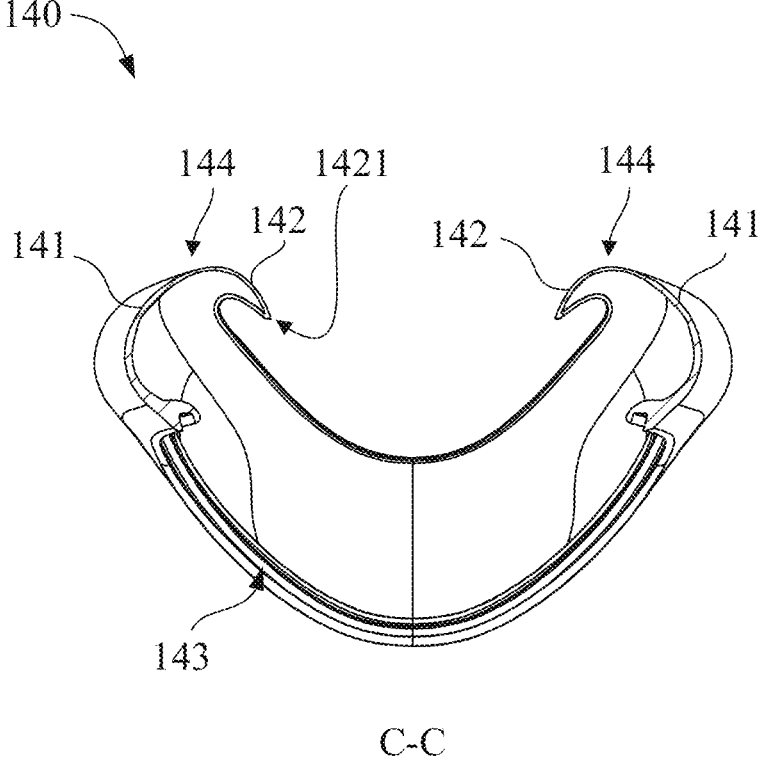
FIG. 10 is a section schematic diagram along section line CC in FIG. 7.

Referring to FIG. 7 to FIG. 10, FIG. 7 shows a front view of a seal forming assembly according to an embodiment of the present invention, FIG. 8 shows a section schematic diagram along section line AA in FIG. 7, FIG. 9 shows a section schematic diagram along section line BB in FIG. 7, and FIG. 10 shows a section schematic diagram along section line CC in FIG. 7. FIG. 7 to FIG. 10 illustrate situations where the thickness of the seal forming assembly 140 exhibits different degrees of change in the thickness in various directions (change in distance). The border 144 (particularly as indicated at a cross-section) indicated in FIG. 8 to FIG. 10 may correspond to a position 144 between the first support area 141 and the second support area 142. The position of the border 144 in FIG. 8 is the closest to the engaging portion 143, the position of the border 144 in FIG. 10 is the second closest to the engaging portion 143, and the position of the border 144 in FIG. 9 is the farthest away from the engaging portion 143. The border 144 indicated in FIG. 8 and FIG. 10 shows that the thickness of the seal forming assembly 140 gradually decreases from the engaging portion 143, and becomes substantially constant at the border 144.

Accordingly, the thickness in the first support area 141 varies, and the second support area 142 is substantially kept at a same thickness. Further, the thickness of an end portion of the second support area 142 in a direction away from the first support area 141 may be configured to increase so as to form an end edge 1421 serving as a rim. Moreover, a vertical distance is present between a position of each point on the engaging portion 143 of the seal forming assembly 140 and the border 144. Among the vertical distances formed, corresponding vertical distances adjacent to cheeks and cheekbones of the patient when in use are greater than corresponding vertical distances adjacent to the nose and the chin of the patient when in use. Because the engaging portion 143 and the border 144 are shaped as curves, the vertical distance is, for example, a vertical distance formed by a distance between a tangent point of a tangent plane on the engaging portion 143 and a tangent point of a corresponding tangent plane on the border 144, along the surface of the seal forming assembly 140. A connecting line between the two tangent points are both perpendicular to the tangent plane on the engaging portion 143 and the corresponding tangent plane on the border 144.

In other embodiments, a position extended from the first support area 141 and of which the thickness gradually decreases to a predetermined thickness is defined as the border 144, and the predetermined thickness may be any value selected from a range of 0.50 mm to 0.70 mm, further providing a wearer with enhanced wearing comfort. Any value within the range 0.50 to 0.70 mm is, for example, any value selected from 0.5, 0.51, 0.52, 0.53, 0.54, 0.55, 0.56, 0.57, 0.58, 0.59, 0.6, 0.61, 0.62, 0.63, 0.64, 0.65, 0.66, 0.67, 0.68, 0.69 and 0.7. Further, with the range above, any value with more digits after the decimal point is also suitable (for example, 0.651, 0.652, . . . ).

Figure 11:
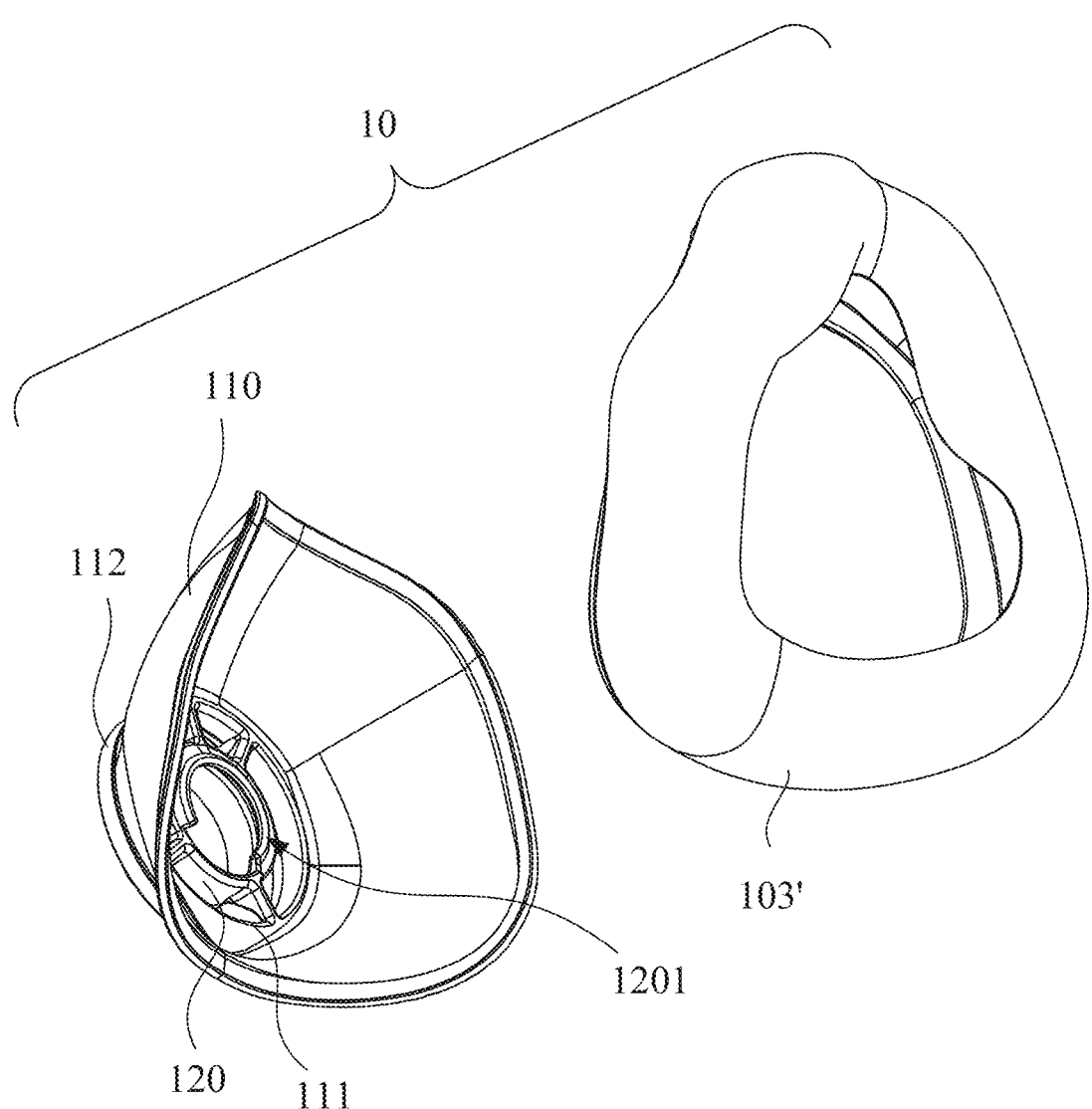
FIG. 11 is a three-dimensional schematic diagram of a cushion assembly in an exploded state according to another embodiment of the present invention.
Figure 12:
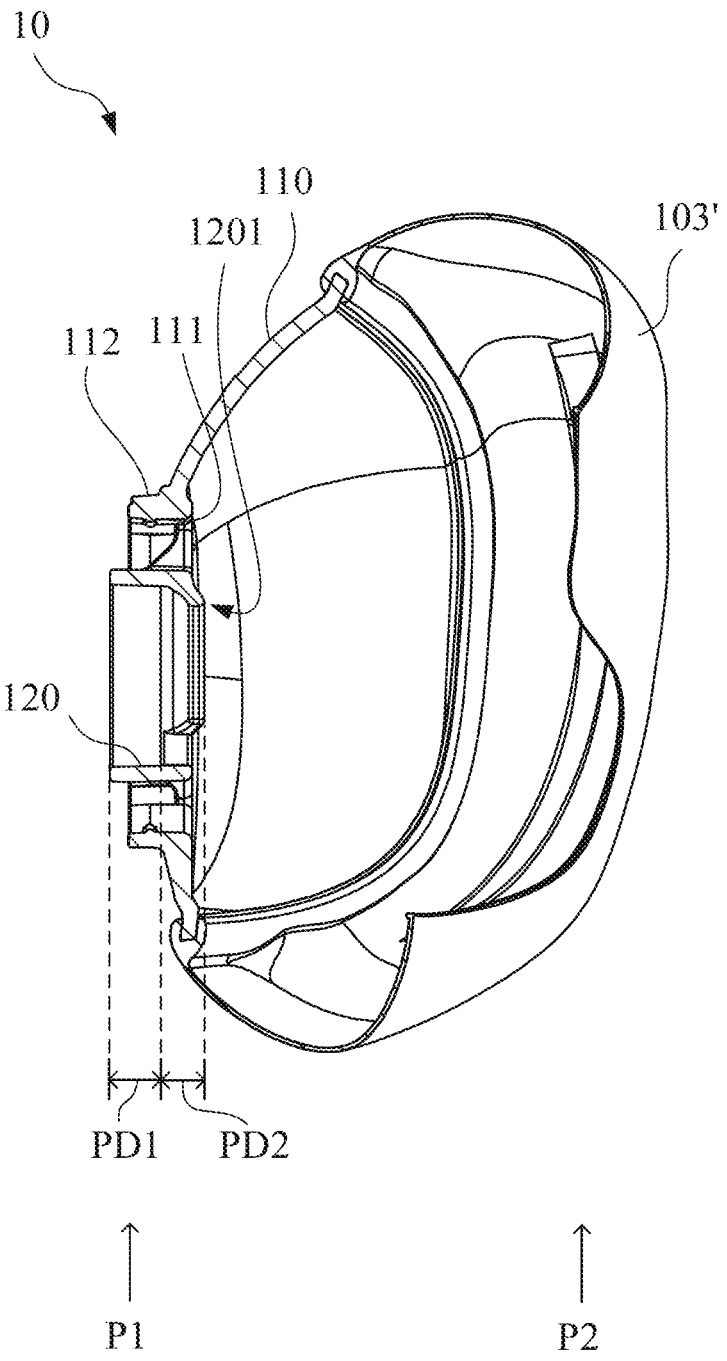
FIG. 12 is a section schematic diagram of the cushion assembly in FIG. 11 in an assembled state.

In other embodiments, the seal forming assembly 140 may further include a channel 145 extending longitudinally on an inner surface (adjacent to the inflating chamber) of two inner edges corresponding to the cheeks of the wearer, and the channel 145 may appear downwardly tapered or a cone having a larger width on the top and a smaller width on the bottom (the bottom of the cone corresponds to the nose of the wearer). The thickness of the channel 145 may be independent from the rule of change in the thickness described above, and the thickness of the channel 145 may be smaller than any adjoining portion, so as to provide better adaptivity with better comfort at the cheeks of the wearer. 4. The Cylindrical Wall of the Cushion Assembly, the Hollow Structure and the Seal Assembly Referring to FIG. 11 and FIG. 12, FIG. 11 shows a three-dimensional schematic diagram of a cushion assembly in an exploded state according to another embodiment of the present invention, and FIG. 12 shows a section schematic diagram of the cushion assembly in FIG. 11 in an assembled state. In this embodiment, the cushion assembly 10 includes a hollow structure 110, a cylindrical wall 120 and a seal assembly 103'.

The hollow structure 110 has a central aperture 111 and a protruding structure 112. The central aperture 111 is structured on a first end P1 of the cushion assembly 10, and provides a route for delivering an air flow when the patient interface is in use. The protruding structure 112 is structured to project from the central aperture 111 in a direction towards the first end P1 of the cushion assembly 10.

The cylindrical wall 120 is provided to the central aperture 111. The cylindrical wall 120 is structured as substantially concentric with the central aperture 111. The cylindrical wall 120 projects in a manner of having a same diameter towards the first end P1 of the cushion assembly 10 by a first distance PD1, and projects in a manner of having different diameters towards a second end P2 opposite to the first end P1 of the cushion assembly 10 by a second distance PD2.

For example, a diameter change within the second distance PD2 may be that the diameter substantially decreases in a direction towards the second end P2; in contrast, a diameter change within the first distance PD1 may be that the diameter substantially stays constant in a direction towards the first end P1. Moreover, in other embodiments, the first distance PD1 may be greater than the second distance PD2.

Referring to FIG. 11 as well as FIG. 12, on the cylindrical wall 120, an eaves portion 1201 having a gradually decreasing diameter in a direction towards the second end P2 may be configured only on a part of an end portion of the cylindrical wall 120, further appearing as a partially encircling eaves portion 1201 of less than 360 degrees. It is observed from FIG. 12 that, under a vertical section line of the partially encircling eaves portion 1201, a partial position at a lower portion of the cylindrical wall 120 does not include the eaves portion 1201. However, when another section line (not shown) perpendicular to the section line in FIG. 12 is used, the eaves portions are present on both upper and lower sides of the cylindrical wall 120. The example shown in FIG. 12 is an eaves portion that encircles by 270 degrees on the end portion of the cylindrical wall 120.

Figure 13:
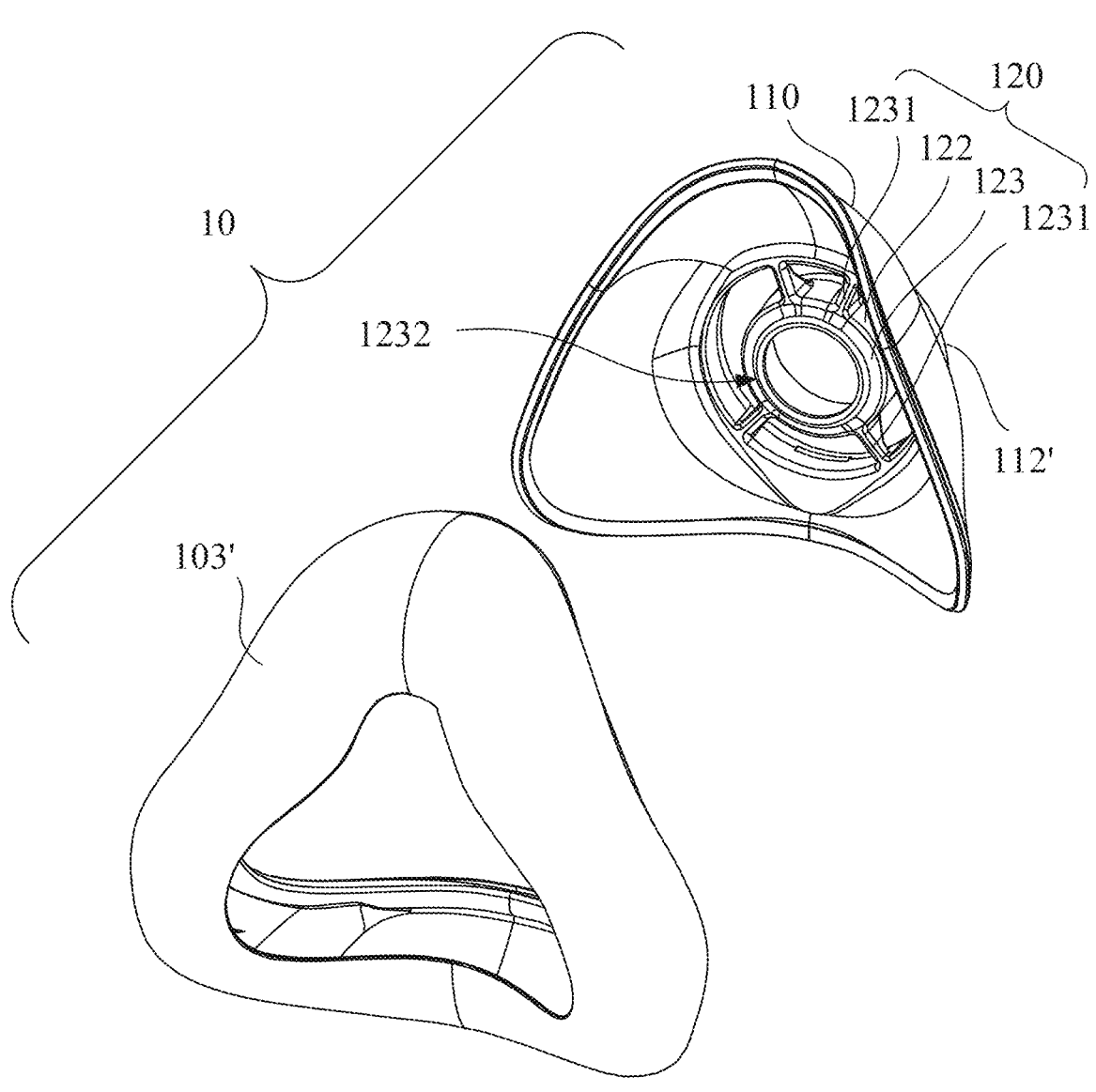
FIG. 13 is a three-dimensional schematic diagram of a cushion assembly according to another embodiment of the present invention.
Figure 14:
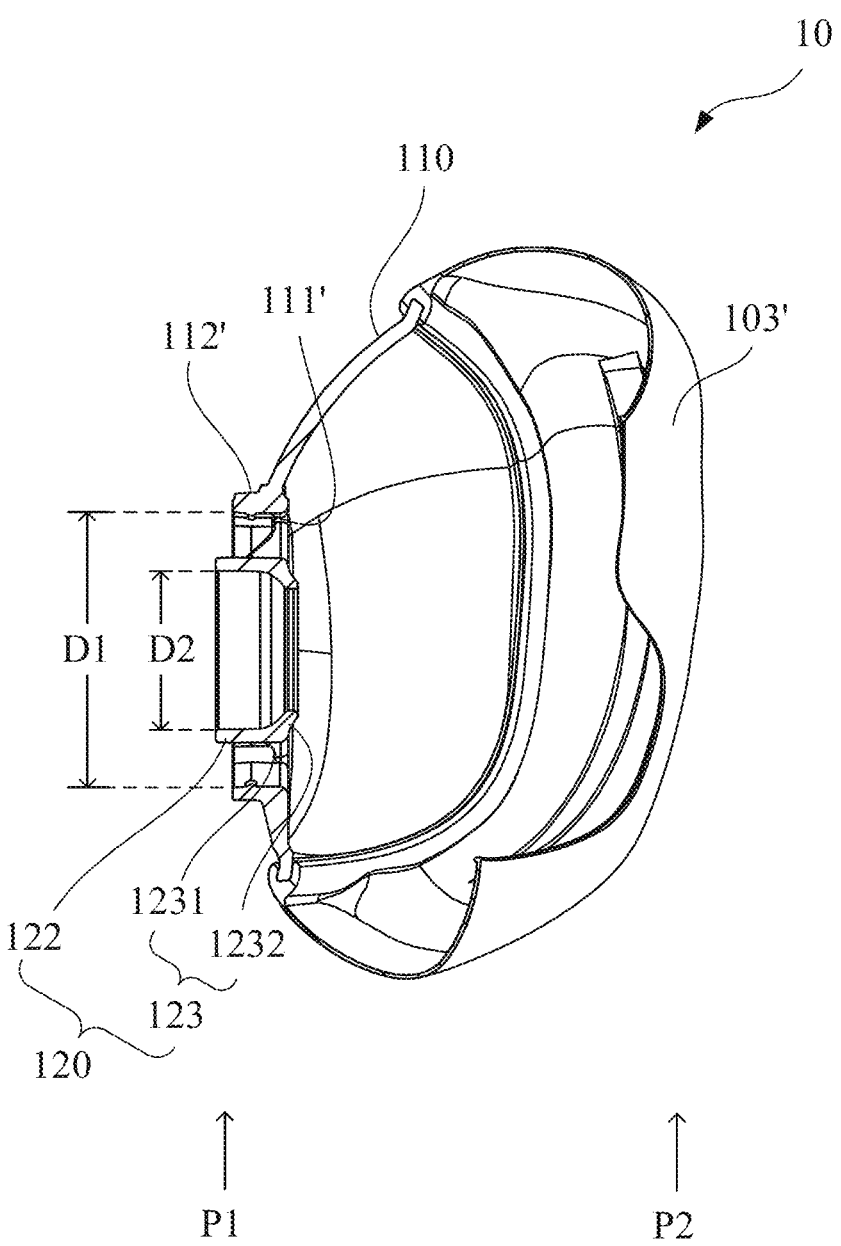
FIG. 14 is a section schematic diagram of the cushion assembly in FIG. 13.

Referring to FIG. 13 and FIG. 14, FIG. 13 shows a three-dimensional schematic diagram of a cushion assembly according to another embodiment of the present invention, and FIG. 14 shows a section schematic diagram of the cushion assembly in FIG. 13. In this embodiment, the cushion assembly 10 includes a hollow structure 110, a cylindrical wall 120 and a seal assembly 103'.

The hollow structure 110 has a cylindrical orifice 111' and a first protruding structure 112'. The cylindrical orifice 111' is structured on a first end P1 of the cushion assembly 10, and is for delivering an air flow when the patient interface is in use. The first protruding structure 112' is structured to project from the cylindrical orifice 111' in a direction towards the first end P1 of the cushion assembly 10.

The cylindrical wall 120 is provided to the cylindrical orifice 111'. The cylindrical wall 120 is structured as substantially concentric with the cylindrical orifice 111'. The cylindrical wall 120 has a second protruding structure 122 and a third protruding structure 123. The second protruding structure 122 projects towards the first end P1 of the cushion assembly 10, and the third protruding structure 123 projects towards a second end P2 opposite to the first end P1 of the cushion assembly 10.

As shown in the embodiment in FIG. 14, the first protruding structure 112' and the second protruding structure 122 are formed as concentric. A diameter D2 of the second protruding structure 122 is smaller than a diameter D1 (an inner diameter as an example in FIG. 14) of the first protruding structure 112'. Moreover, the third protruding structure 123 has a first section 1231 and a second section 1232. The first section 1231 appears as a stalk form, and the second section 1232 appears as a head form that is supported by the first section 1231. The first section 1231 in a stalk form is provided on the cylindrical wall 120 and is in flow communication with the cylindrical orifice 111'. The head of the second section 1232 is substantially truncated hollow cone, and has a relatively narrow top end so as to extend into the hollow structure 110.

Moreover, compared to the eaves portion 1201 partially encircling by 270 degrees shown in FIG. 12, the eaves portion encircling by 360 degrees in form of a truncated hollow cone is shown in the exemplary embodiments in FIG. 13 and FIG. 14. The second section 1232 appearing as a truncated hollow cone has a diameter smaller than the diameter D2 (an inner diameter as an example in FIG. 14) of the second protruding structure 122. On the basis of the structural features of the first to third protruding structures above, they may also be referred to as first to third protruding ring structures, wherein the hollow structure 110 may be formed by a single material. On the other hand, a seal assembly 103' is configured to be in a soft material relative to the hollow structure 110.

As shown in FIG. 13 and FIG. 14, the first section 1231 in a stalk form may be regarded as a support structure, such that the cylindrical wall 120 can be provided to an opening part (the cylindrical orifice 111') of the hollow structure 110 and be concentric with the opening part (the cylindrical orifice 111').

Figure 15:
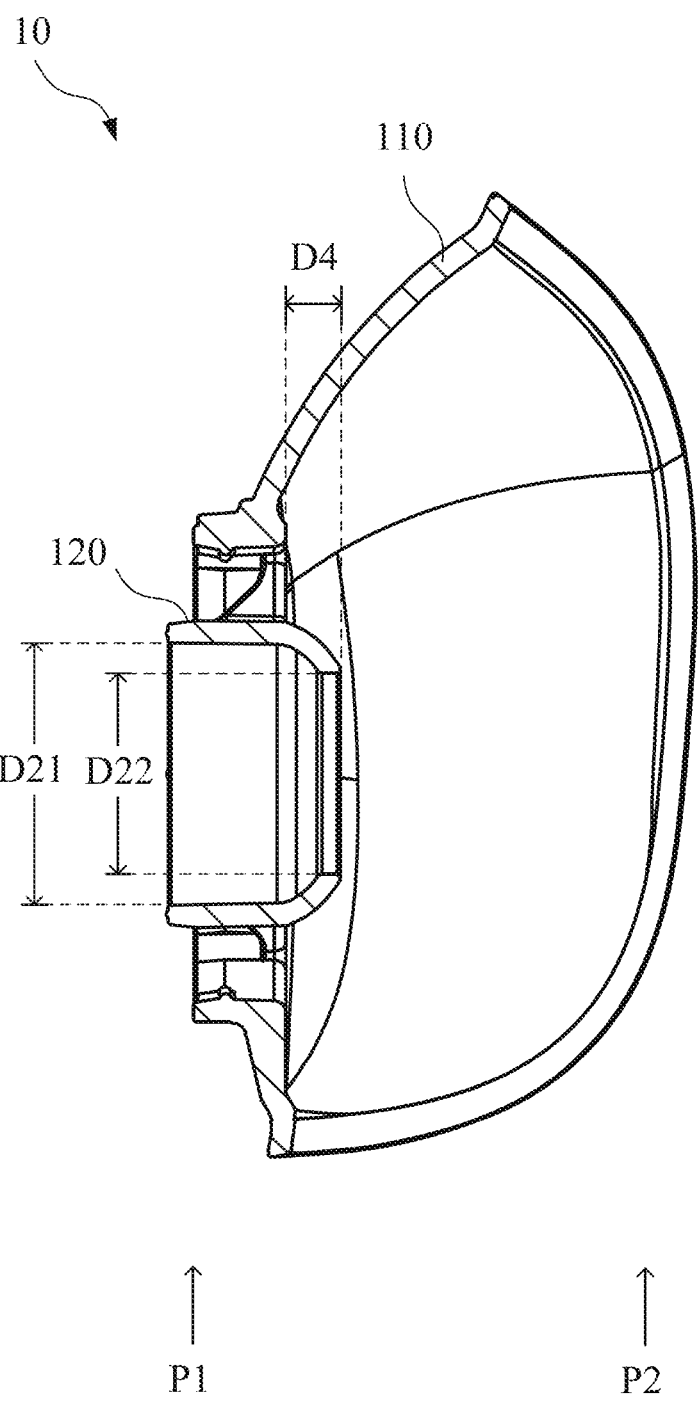
FIG. 15 is a section schematic diagram of a cushion assembly according to another embodiment of the present invention.

Referring to FIG. 15, FIG. 15 shows a section schematic diagram of a cushion assembly according to another embodiment of the present invention. An inner diameter of the cylindrical wall 120 before a change is an initial diameter D21, and the inner diameter of the cylindrical wall 120 after the change is a reduced diameter D22. The cylindrical wall 120 extends into the hollow structure 110 by an extent of a depth D4. In FIG. 15, a distance by which the cylindrical wall 120 changes from the initial diameter D21 to the reduced diameter D22 is longer, and the cylindrical wall 120 can be extended more into the hollow structure 110. Accordingly, compared to the cylindrical wall 120 shown in FIG. 14, the cylindrical wall 120 in FIG. 15 has a more moderate change in the diameter and extends into the hollow structure 110 by a deeper extent. Thus, in the direction towards the second end P2 of the cushion assembly 10, an inner wall surface of the cylindrical wall 120 may exhibit a more moderate curved surface or inclined surface.

5. The Structure of the Headgear Assembly

Figure 16:
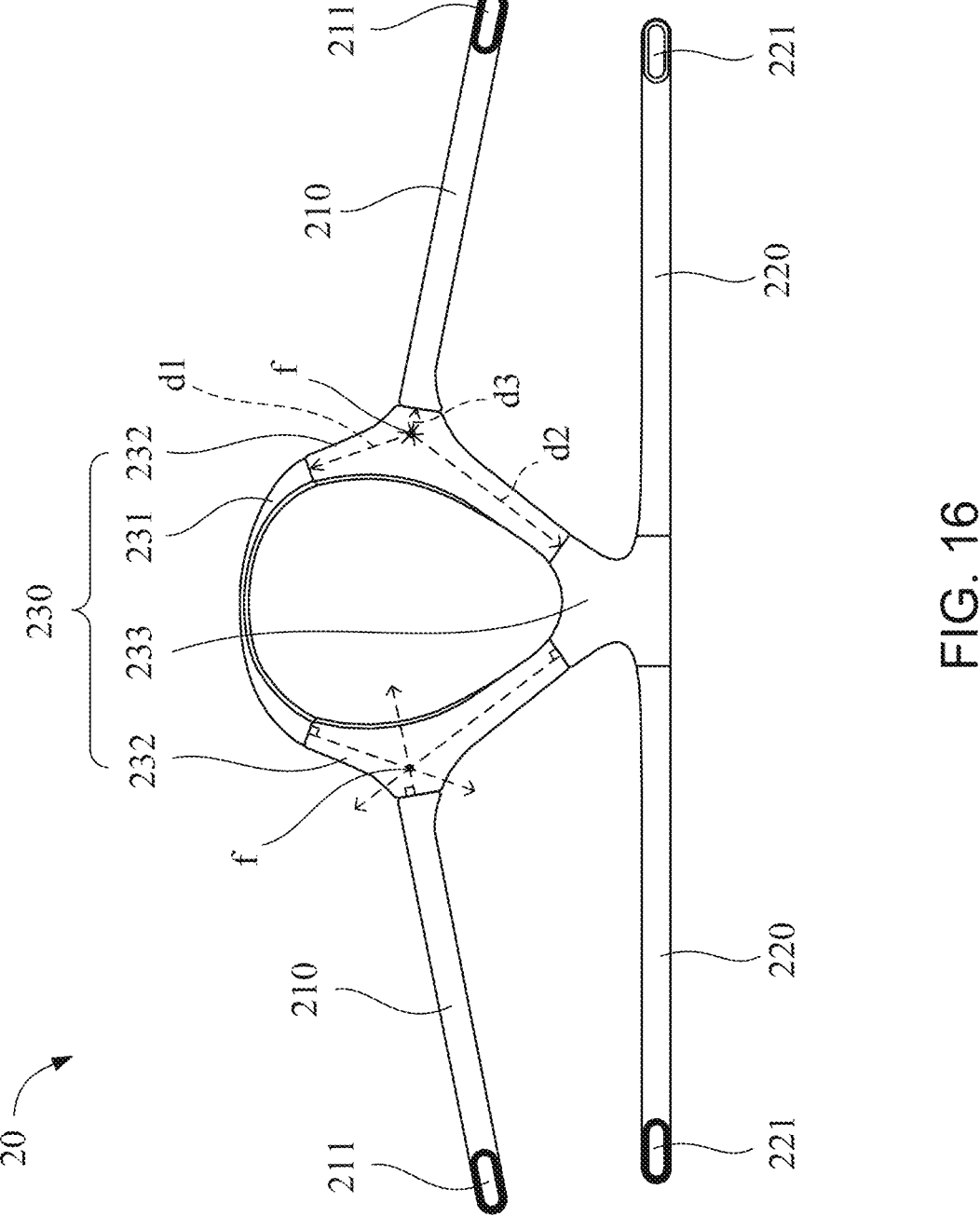
FIG. 16 is a three-dimensional schematic diagram of a headgear assembly according to an embodiment of the present invention.
Figure 17:
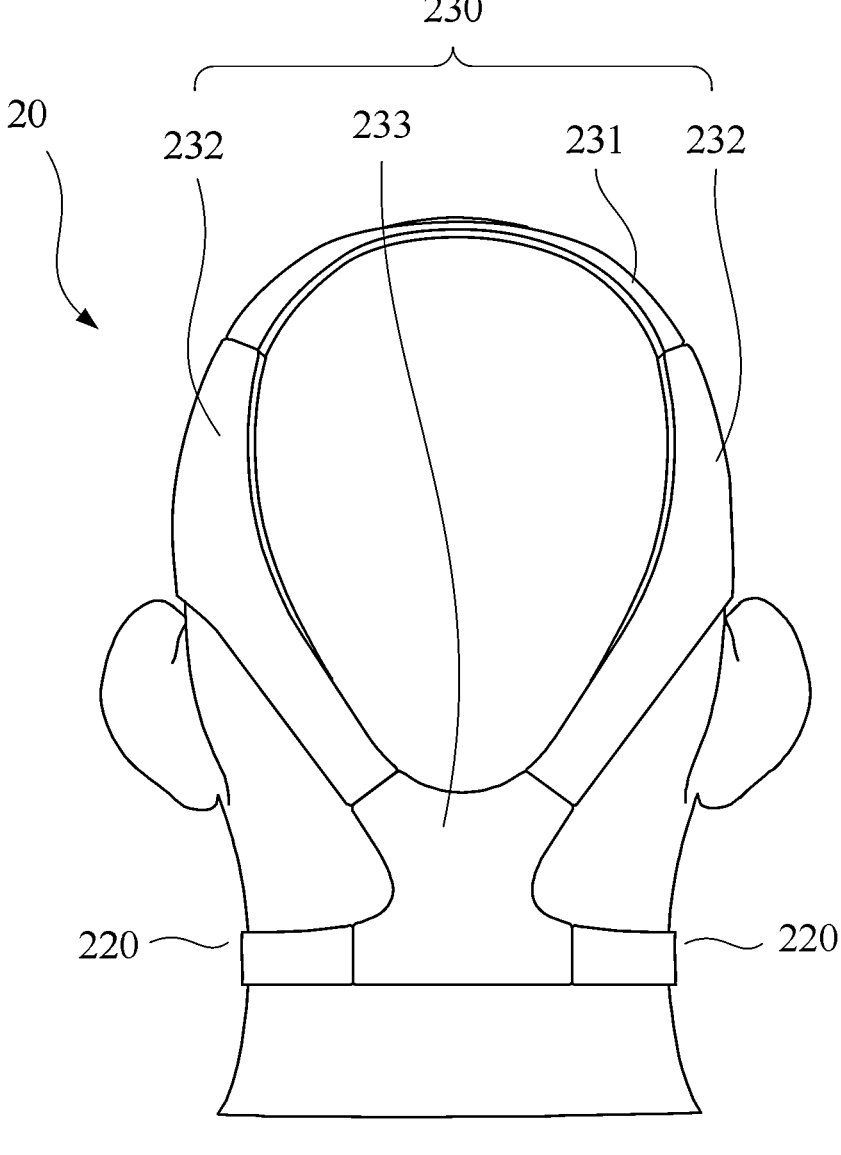
FIG. 17 is a schematic diagram of the headgear assembly in FIG. 16 worn at a head of a patient.

Referring to FIG. 16 and FIG. 17 as well as FIG. 2, FIG. 16 shows a three-dimensional schematic diagram of a headgear assembly according to another embodiment of the present invention, and FIG. 17 shows a schematic diagram of the headgear assembly in FIG. 16 worn at a head of a patient.

The headgear assembly 20 includes a plurality of straps, and these straps are for adjusting the position of the patient interface when the patient interface is worn by a patient, allowing the patient interface to be stably and comfortably secured at the head of the patient, and to form an air flow space, breathing chamber or inflating chamber on a face of the patient to apply a treatment pressure to airways of the patient. These straps include a plurality of upper straps 210, a plurality of lower straps 220, and a rear portion configured to reach at least a part of an occipital bone of the patient when in use, wherein the rear portion is referred to as a rear strap assembly 230.

The upper straps 210 include straps extendable to above ears of the applying patient, and the lower straps 220 include straps extendable to below the ears of the applying patient (referring to FIG. 17). The rear strap assembly 230 includes a top portion 231, a plurality of side portions 232 and a bottom portion 233. Referring to FIG. 2 and FIG. 3, the frame assembly 50 is adapted to correspond to the attachment of the upper straps 210, and a position of the attachment is, for example, the slits 501 of the frame assembly 50 and located on upper edges of two sides. Moreover, the frame assembly 50 is adapted to correspond to the attachment of the lower straps 230, and a position of the attachment is, for example, the lower straps 220 correspondingly attached by the corresponding headgear clips 30 engaged with the slits 501 at lower edges on the two sides of the frame assembly 50.

As shown in FIG. 16 an FIG. 17, the top portion 231 of the rear strap assembly 230 is provided between the side portions 232, and the bottom portion 233 of the rear strap assembly 230 is provided between the side portions 232 and the lower straps 220. The bottom portion 233 of the rear strap assembly 230 may be simultaneously connected to the side portions 232 and the lower straps 230, and the upper straps 210 are provided on one side corresponding to the side portions 232. The upper straps 210 include upper strap attaching portions 211 on ends connected to the corresponding side portions 232, and the lower straps 220 include lower strap attaching portions 221 on ends opposite to the ends connected to the corresponding lower portion 233. The upper strap attaching portions 211 and the lower strap attaching portions 221 are secured on the frame assembly 50 and/or secured on the headgear clips 30 by means of attachment. The upper strap attaching portions 211 and the lower strap attaching portions 221 are, for example, parts with felting effects, such as hook-and-eye straps (for fastening to surfaces of the upper straps 210 or the lower straps 220).

As shown in FIG. 16, each of the side portions 232 has an intersection point f. Between the intersection point f of each side portion 232 and the top portion 231 is a first strap distance d1, between the intersection point f of each side portion 232 and the lower portion 233 is a second strap distance d2, and between the intersection point f of each side portion and the upper strap 210 is a third strap distance d3. In one implementation aspect, the first strap distance d1 is smaller than the second strap distance d2, and in another implementation aspect, the first strap distance d1 is also greater than the third strap distance d3.

The intersection point f of each side portion 232 is a geometric center of the side portion. In a preferred embodiment, each side portion 232 has a junction from the top portion 231, the upper straps 210 and the lower portion 233, and three perpendicular segments from the intersection point f to the junction may commonly intersect at the intersection point f. With the configuration condition forming the intersection point f, the pressure imposed by the headgear assembly 20 on the head of a wearer or a patient can be appropriately distributed to improve wearing comfort.

Figure 18:
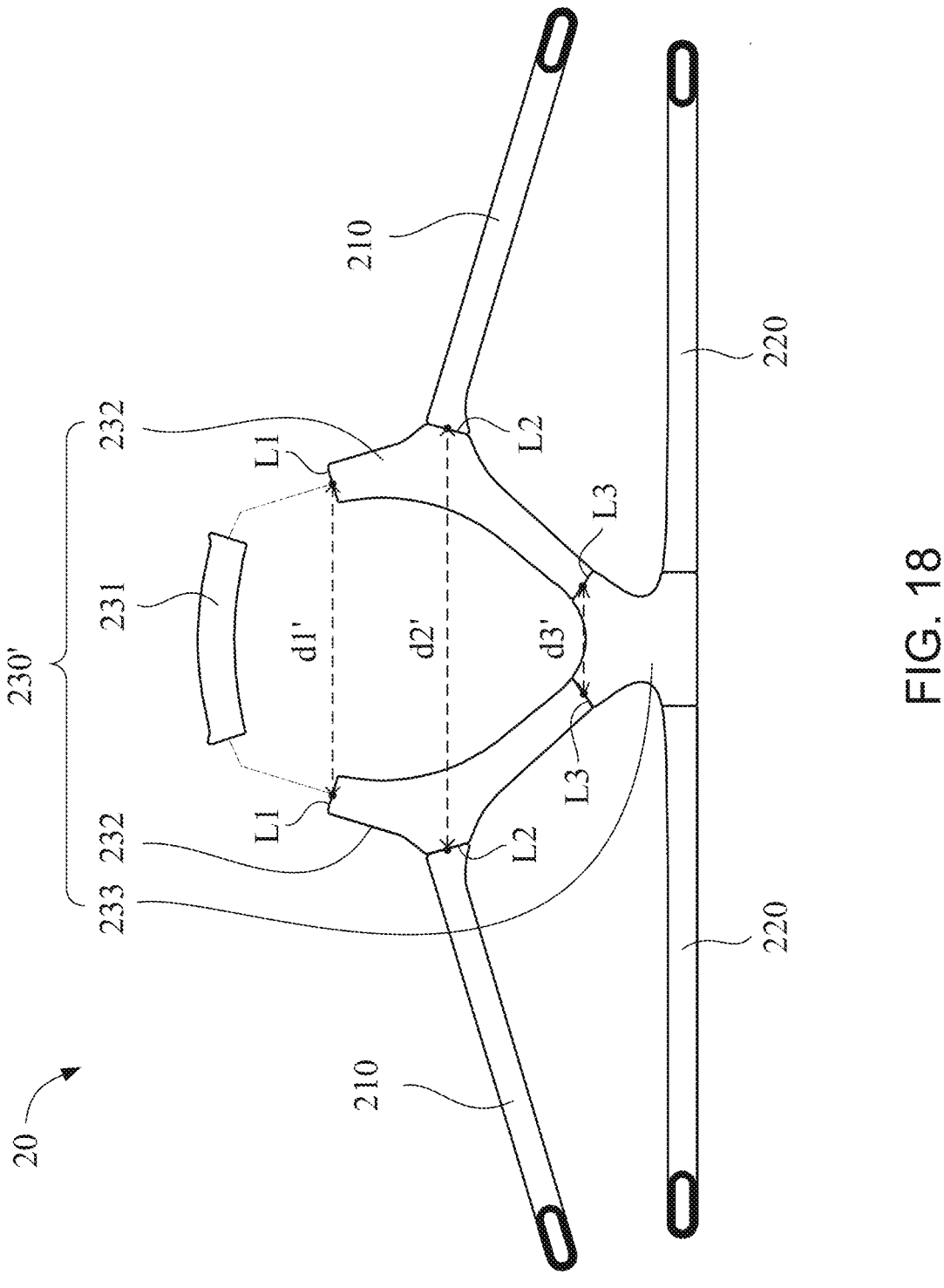
FIG. 18 is a three-dimensional schematic diagram of a headgear assembly according to another embodiment of the present invention.

FIG. 18 shows a three-dimensional schematic diagram of a headgear assembly according to another embodiment of the present invention. The headgear assembly 20 includes a plurality of straps, and these straps are for adjusting the position of the patient interface when the patient interface is worn by a patient. These straps include a plurality of upper straps 210, a plurality of lower straps 220, and a rear portion 230' configured to reach at least a part of an occipital bone of the patient when in use.

The rear strap assembly 230' includes a top portion 231, a plurality of side portions 232 and a bottom portion 233. The top portion 231 is provided between the side portions 232, the bottom portion 233 is provided between the side portions 232 and the lower straps 220, and the upper straps 210 are provided to the corresponding side portions 232. Between each side portion 232 and the top portion 231 is a engaging line 11, between each upper strap 210 and the corresponding side portion 232 is a second engaging line L2, and between each side portion 232 and the bottom portion 233 is a third engaging line L3.

A distance between centers of two first engaging lines L1 is a first strap gap d1'. A distance between centers of two second engaging lines L1 is a second strap gap d2'. A distance between centers of two third engaging lines L1 is a third strap gap d3'. In one implementation aspect, the first strap gap d1' is smaller than the second strap gap d2' and greater than the third strap gap d3'.

6. The Structure of the Elbow Assembly

Figure 19:
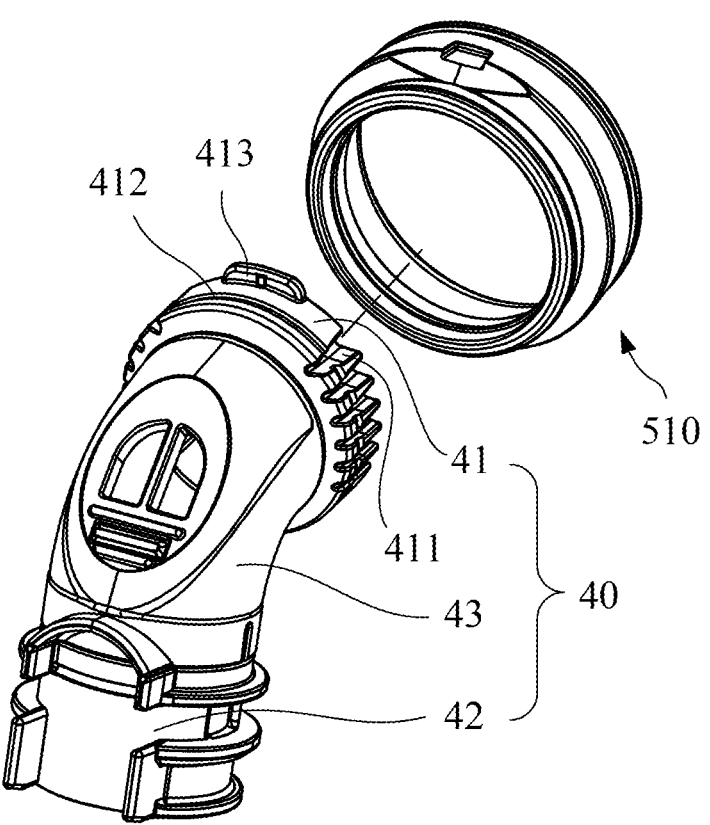
FIG. 19 is a three-dimensional schematic diagram of an elbow assembly and a transition ring structure in an exploded state according to another embodiment of the present invention.
Figure 20:
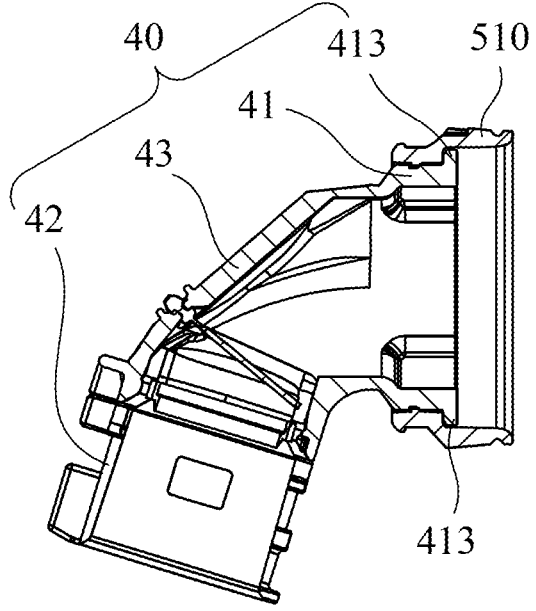
FIG. 20 is a section schematic diagram of the elbow assembly and the transition ring structure in FIG. 19 in an assembled state.

Referring to FIG. 19 and FIG. 20, FIG. 19 shows a three-dimensional schematic diagram of an elbow assembly and a transition ring structure in an exploded state according to another embodiment of the present invention, and FIG. 20 shows a section schematic diagram of the elbow assembly and the transition ring structure in FIG. 19 in an assembled state. The elbow assembly 40 is provided to the transition ring structure 410, and is rotatable by 360 degrees relative to the elbow assembly 40. The elbow assembly 40 includes a first end 41, a second end 42 and a body 43.

The body 43 of the elbow assembly 40 includes a conduit air pathway capable of adjusting a direction of an air flow. The body 43 defines, by a bent inner wall, the conduit air pathway producing a turning effect on the air flow being delivered, further generating a route adjustment effect on the air flow flowing through the elbow assembly 40. Thus, the air flow (referring to FIG. 1) delivered from the flow generator (not shown) through the air delivery tube 60 enters the elbow assembly 40 through the second end 42 of the elbow assembly 40, passes through the conduit air pathway in the body 43 of the elbow 43 to cause a change in the delivery direction of the air flow, and is then discharged from the first end 41 to form the route of the air flow delivered towards the air flow space, breathing chamber or inflating chamber as described above.

7. The Structure of the Vent Assembly

Figure 21:
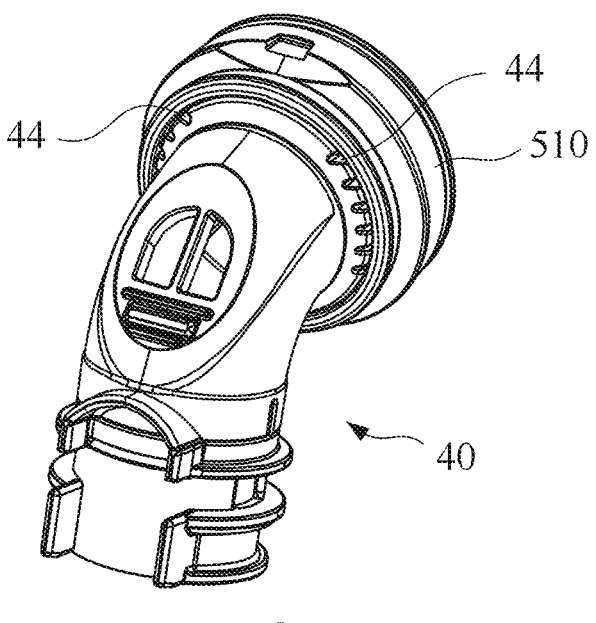
FIG. 21 is a section schematic diagram of the elbow assembly and the transition ring structure in FIG. 19 in an assembled state from another perspective.

Referring to FIG. 19 and FIG. 21, FIG. 21 shows a section schematic diagram of the elbow assembly and the transition ring structure in FIG. 19 in an assembled state from another perspective. A curved outer structure of the first end 41 of the elbow assembly 40 may included a plurality of concavities 411 formed on an outer surface of the first end 41. When the elbow assembly 40 and the transition ring structure 510 are in an assembled state, the concavities 411 and at least a part of the transition ring structure 510 may together form air pathways 44 (or referred to as exhaust ducts). As shown in FIG. 21, the concavities 411 and an inner wall surface of the transition ring structure 510 together form passages for air to pass through, and these passages are in communication with the air flow space, breathing chamber or inflating chamber above, further allowing air exhaled by the patient to be discharged through the passages to the ambient environment.

As shown in FIG. 19, an outer surface of the first end 41 of the elbow assembly 40 may further include ring groove 412 and a blocking portion 413. The ring groove 412 is structured to encircle on the outer surface of the first end 41, and crosses the concavities 411. The ring groove 412 is structured to match with the inner surface of the transition ring structure 510. Once the elbow assembly 40 is assembled to the transition ring structure 510 in a non-detachable manner by the ring groove 412, the elbow assembly 40 is rotatable relative to the transition ring structure 510 on a plane. Moreover, the blocking portion 413 may be provided on both upper and lower ends of the first end 41 of the elbow assembly 40. Once the elbow assembly 40 is provided on the transition ring structure 510, the at least one blocking portion 413 stops the elbow 40 from departing from the transition ring structure 510 to form a non-releasable arrangement.

Figure 22:
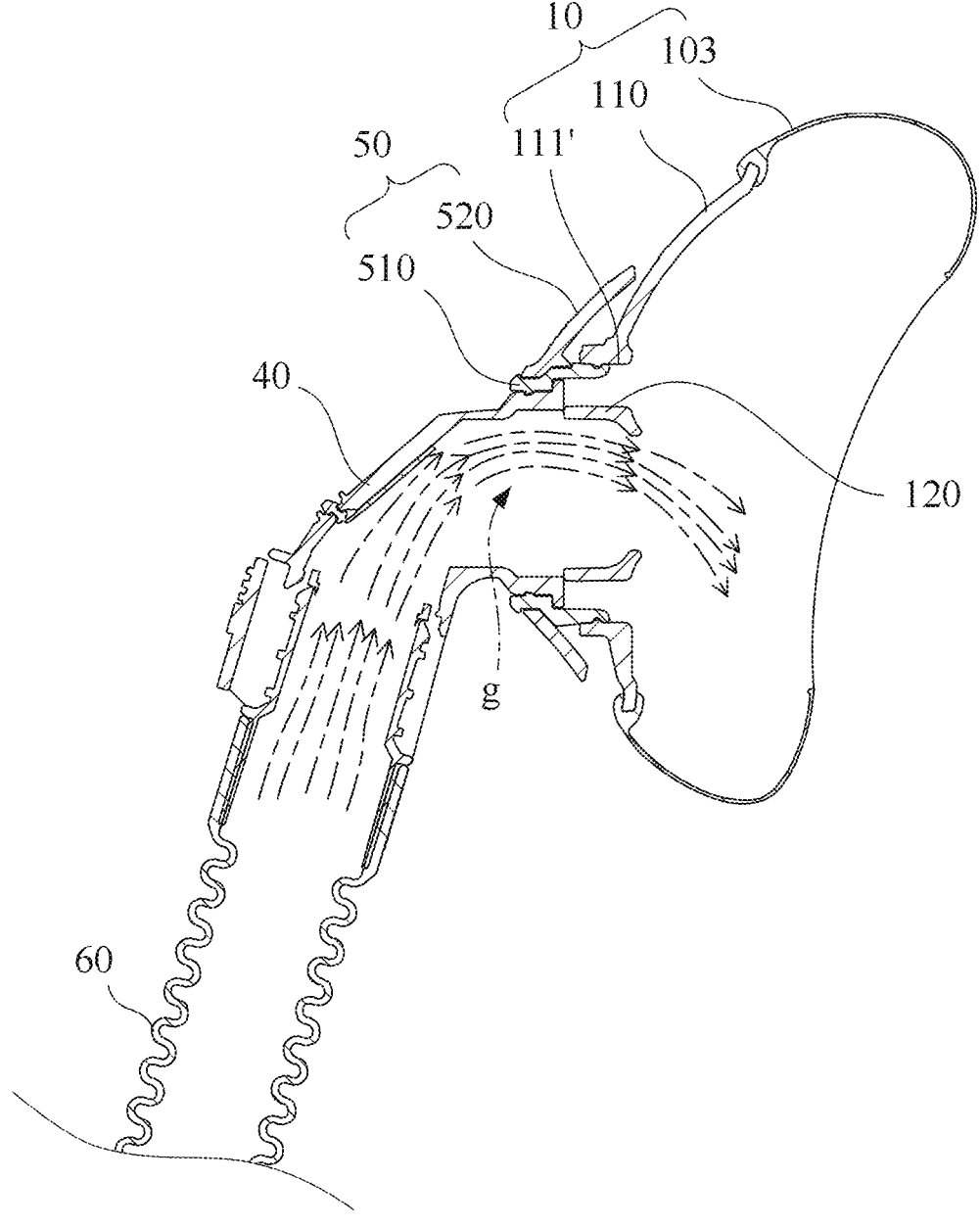
FIG. 22 is a section schematic diagram of a patient interface according to another embodiment of the present invention.
Figure 23:
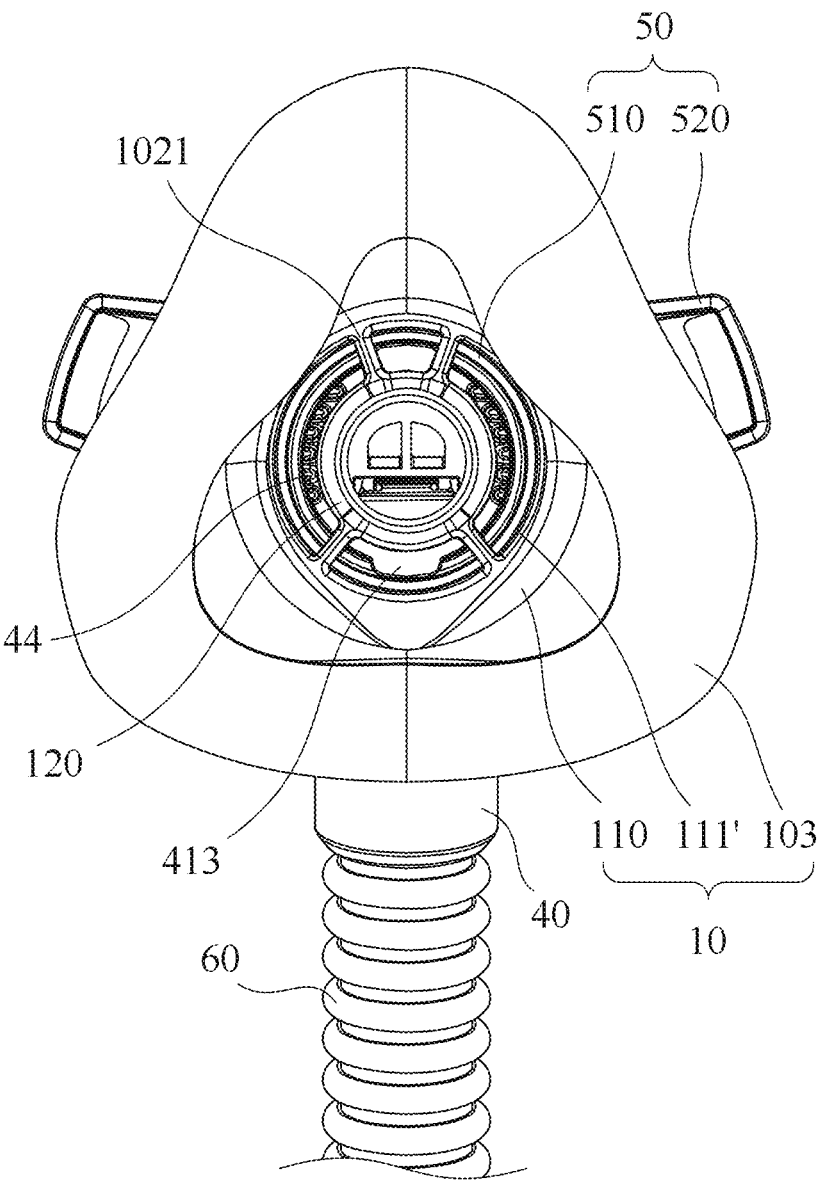
FIG. 23 is a three-dimensional schematic diagram of the patient interface in FIG. 22 from another perspective.

Referring to FIG. 22 and FIG. 23, FIG. 22 shows a schematic diagram of a patient interface according to another embodiment of the present invention, and FIG. 23 shows a three-dimensional schematic diagram of a patient interface in FIG. 22 from another perspective. The cylindrical wall 120 is provided in the cylindrical orifice 111' of the cushion assembly 10 by a plurality of support structures 1021, wherein the support structures 1021 are in flow communication with the cylindrical orifice 111'. One end of each of the support structures 1021 is connected to the outer surface of the cylindrical wall 120, and the other end of each of the support structures 1021 is connected to the inner surface of the cylindrical orifice 111' (referring to FIG. 13 and FIG. 14).

As shown in FIG. 23, the support structures 1021 are in an asymmetric arrangement relative to an axis of the cylindrical wall 120, wherein the axis is a central axis (a vertical line perpendicular to the drawing) of the cylindrical wall 120. The asymmetrical arrangement of the support structures 1021 are, for example, an arrangement in which two adjacent support structures 1021 with a shortest gap in between along the outer surface of the cylindrical wall 120 can correspond to positions of a nose of the patient wearing the patient interface in use.

As shown in FIG. 22, the transition ring structure 510 provides attachment of the headgear secure assembly 520, the elbow assembly 40 and the cushion assembly 10, and allows the headgear secure assembly 520, the elbow assembly 40 and the cushion assembly 10 to have a non-direct engagement relation. Moreover, the elbow assembly 40 is used for outputting air to an end portion of the first end 41 via the transition ring structure 510, and can coordinate with one end of the cylindrical wall 120 of the cushion assembly 10 to form an air duct for passing and delivering an air flow to a rear end. Gas exhaled by the patient may be guided to the air pathways 44 (referring to FIG. 23) for gas wash-out, so as to form a state of flow field diversion of the air flow.

Since an air flow turns and is deflected in the body 43 of the elbow assembly 40, a region where the air flow is denser could be formed at a turning position during a flowing process of the air flow. As shown in FIG. 22, the elbow assembly defines, by the bent inner wall, a conduit air pathway that causes most of a delivered air flow g to be gathered on an upper portion. Most of the incoming air flow delivered from the flow generator to the breathing chamber may pass through the conduit air pathway and the inner surface of the cylindrical wall 120 of the cushion assembly 10. An eaves structure on the other end of the cylindrical wall 120 further provides the flow field of the air flow with guidance. The eaves structure (a part projecting towards the second end of the cushion assembly 10) of the cylindrical wall 120 can change the direction of outgoing air flow for the air flow delivered from the elbow assembly 40, such that the direction of the outgoing air flow is adjusted downwards.

Thus, the eaves structure of the cylindrical wall 120 causes a main air flow mostly gathered on the upper portion of the conduit air pathway to exit from the cylindrical wall 120 in an outgoing direction that non-parallel to the axis of the cylindrical wall 120. Therefore, the degree of impact imposed by the air flow on the mouth and nose of the patient can be alleviated, and the air flow exhaled by the patient when in use is enabled to smoothly flow to the upper portion of the air flow space, breathing chamber or inflating chamber and further be discharged via the air pathways (exhaust ducts) to the ambient environment.

8. Engagement and Positions of the Headgear Assembly and the Headgear Secure Assembly As shown in FIG. 5, the headgear assembly 20 is secured in the patient interface by the headgear secure assembly 520 and the headgear clips 30. The headgear attachment portions 522 of the headgear secure assembly 520 are for attaching the corresponding headgear clips 30, and the straps corresponding to the headgear assembly 20 are then secured to the headgear secure assembly 520 by the headgear clips 30. The upper opening 521 of the headgear secure assembly 520 is for attaching the corresponding strap of the headgear assembly 20.

Figure 24:
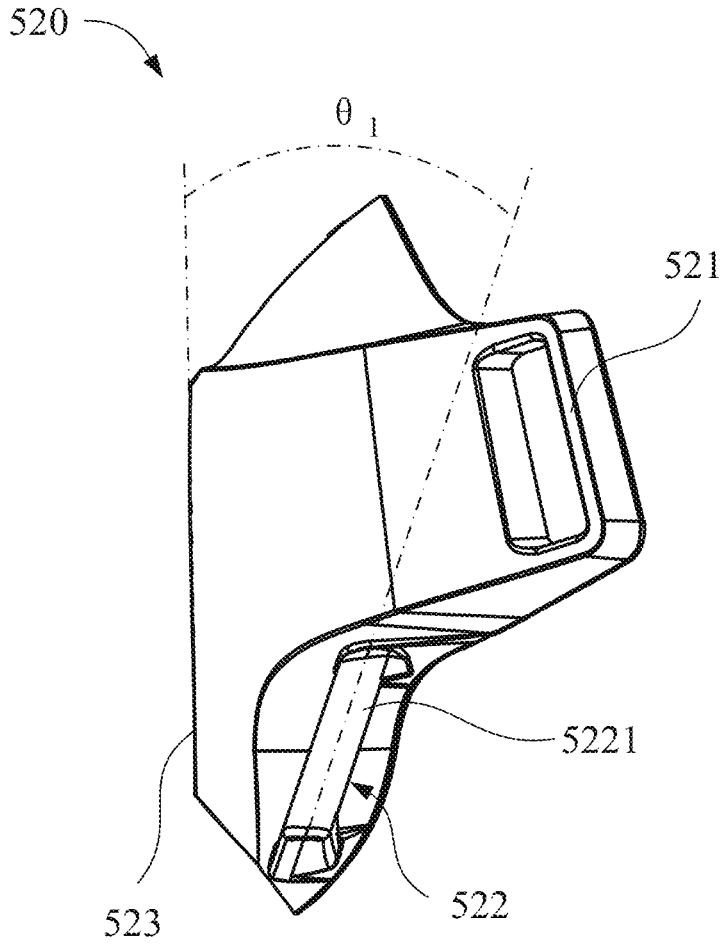
FIG. 24 is a three-dimensional schematic diagram of a headgear secure assembly according to another embodiment of the present invention.

Refer to FIG. 24 showing a three-dimensional schematic diagram of a headgear assembly according to another embodiment of the present invention. The headgear attachment portion 522 has an attachment pin 5221, which can be used for attaching the corresponding headgear clip 30. With respect to the opening plane formed by the central opening 523 of the headgear secure assembly 520, a center axis of the attachment pin 5221 forms an inclined angle θ1 relative to the opening plane. The inclined angle θ1, that is, an included angle of the opening plane formed relative to the central opening 523 in a clockwise direction, can be between 18 and 22 degrees, and preferably is configured at an angle between 20.5 and 20.7 degrees.

Figure 25:
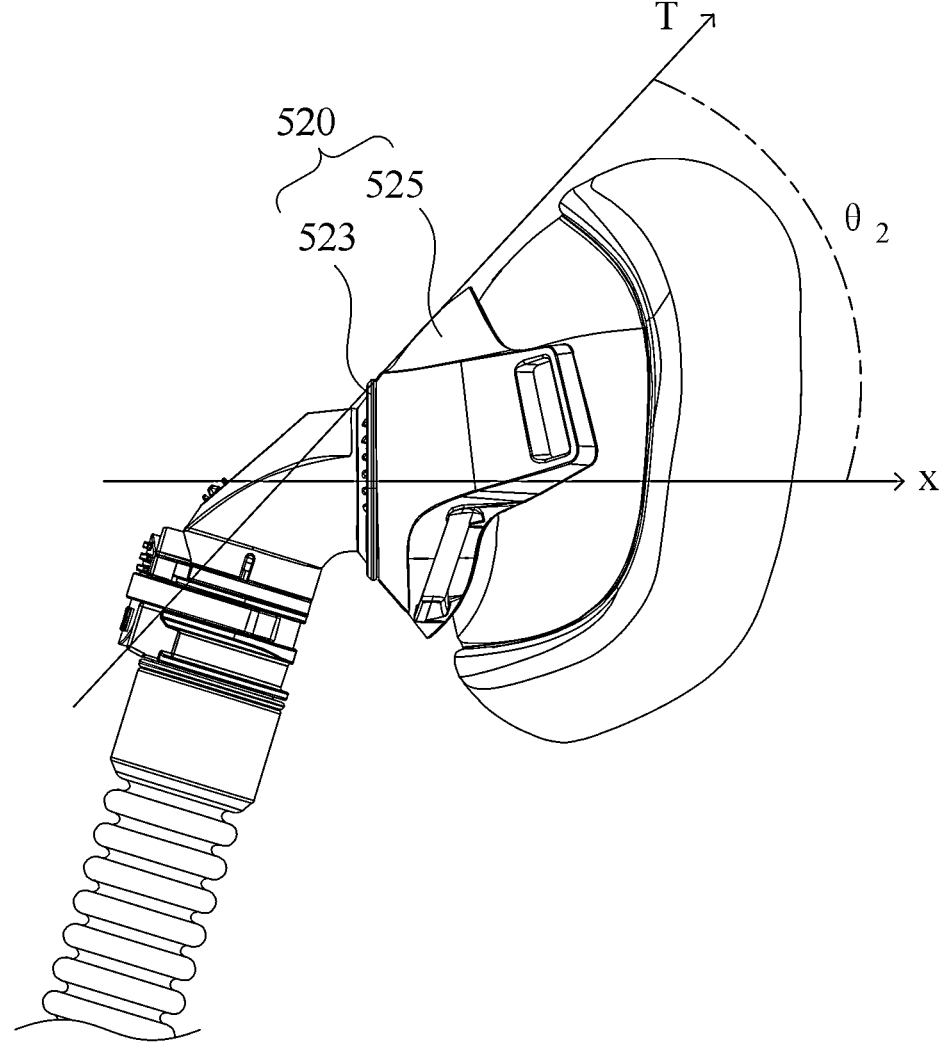
FIG. 25 is a three-dimensional schematic diagram of a patient interface according to another embodiment of the present invention.

Refer to FIG. 25 showing a three-dimensional schematic diagram of a patient interface according to another embodiment of the present invention. The headgear secure assembly 520 includes an upper cover 525 extended in a direction oblique from the central opening 523 towards a rear end. The upper cover 525 is in a lifted manner, and a lifted angle 82 formed by such degree of lifting between a tangent T of the upper cover 525 and a center axis X of the central opening 523 is between 42 and 48 degrees.

Figure 26:
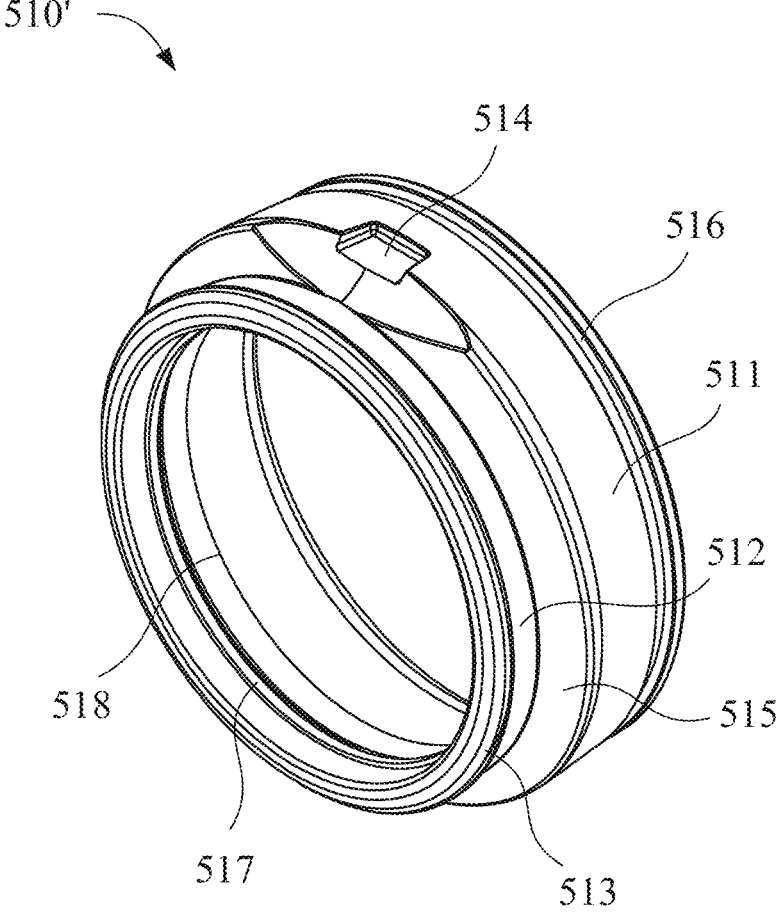
FIG. 26 is a three-dimensional schematic diagram of a connecting ring structure according to an embodiment of the present invention.
Figure 27:
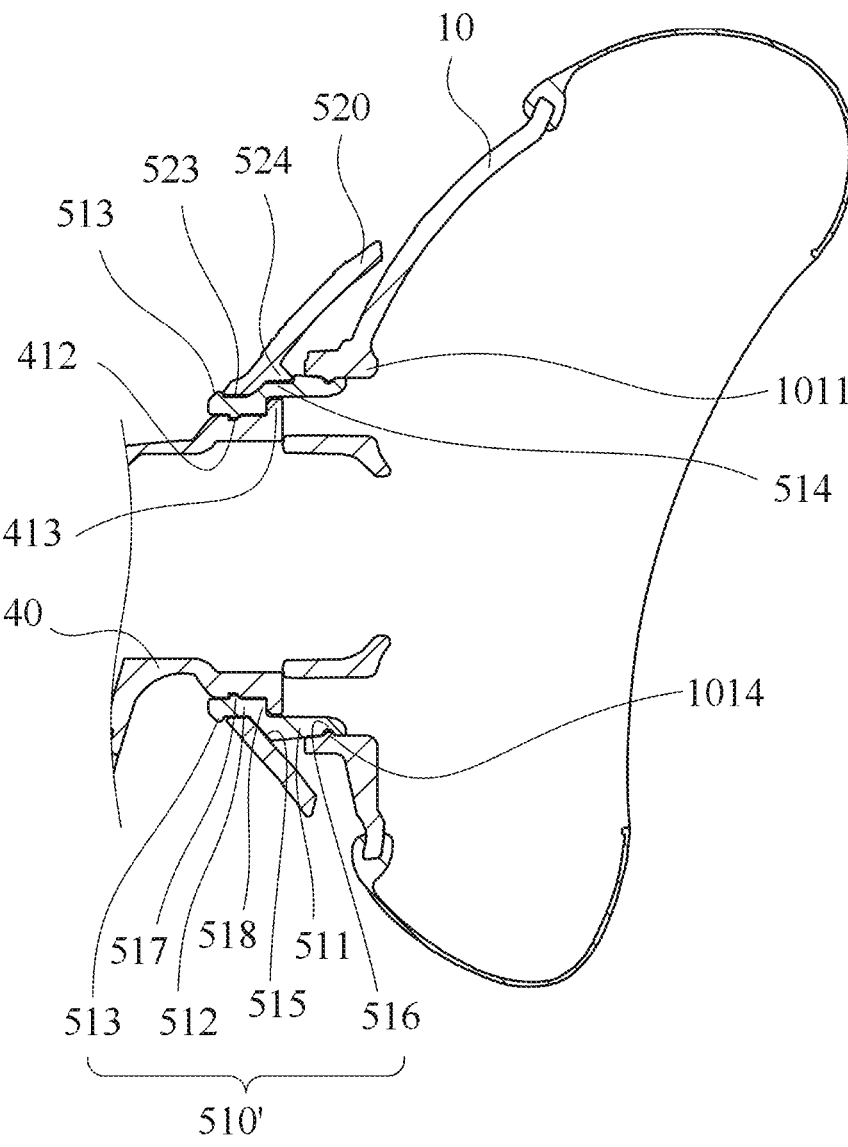
FIG. 27 is a section schematic diagram of the connecting ring structure in FIG. 26 in a state of use.
Figure 28:
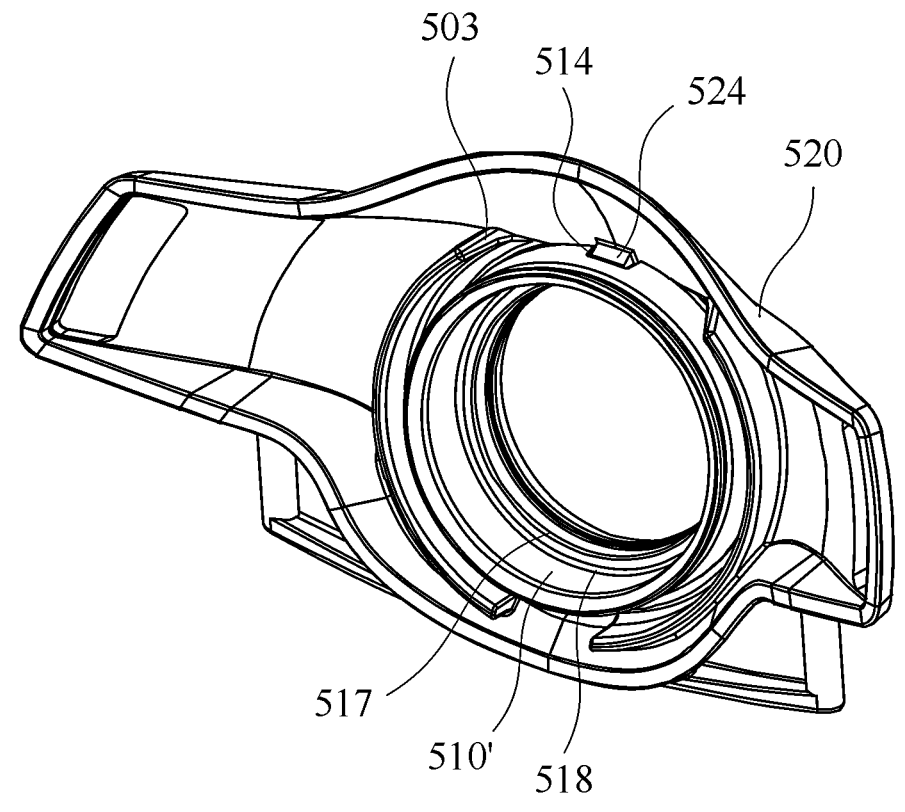
FIG. 28 is a three-dimensional schematic diagram of the connecting ring structure in FIG. 26 in a state of use.

9. Engagement and Sealing of the Headgear Assembly, the Elbow Assembly and the Headgear Secure Assembly Referring to FIG. 26, FIG. 27 and FIG. 28, FIG. 26 shows a three-dimensional schematic diagram of a connecting ring structure according to an embodiment of the present invention, FIG. 27 shows a section schematic diagram of the connecting ring structure in FIG. 26 in a state of use, and FIG. 28 shows a three-dimensional schematic diagram of the connecting ring structure in FIG. 26 in a state of use. A connecting ring structure 510' (or referred to as a transition ring structure) has a first ring portion 511 and a second ring portion 512. An inner diameter of the first ring portion 511 is greater than an inner diameter of the second ring portion 512. An outer diameter of the first ring portion 511 is also greater than an outer diameter of the second ring portion 512.

The second ring portion 512 is accommodated in the central opening 523 of the headgear secure assembly 520. The second ring portion 512 has on an end edge thereof an interference structure 513 that projects radially outwards. An outer diameter of the second ring structure 512 at a position of the interference structure 513 is slightly greater than a diameter of the central opening 523 of the headgear secure assembly 520, and an outer diameter at a middle section of the second ring portion 512 is slightly smaller than the diameter of the central opening 523 of the headgear secure assembly 520, so as to fasten the connecting ring structure 510' on the headgear secure assembly 520.

The connecting ring structure 510' has a first limiting portion 514, which correspondingly interferes a second limiting portion 524 on the headgear secure assembly 520. A width of the first limiting portion 514 is slightly greater than a width of the second limiting portion 524, such that the headgear secure assembly 520 and the connecting ring structure 510' are rotatable relative to each other within a limit. Together by the interference structure 513 and a bottom edge of the first limiting portion, and a transition surface 515 between the first ring portion 511 and the second ring portion 512, the headgear secure assembly 520 is held on the connecting ring structure 510'. The transition surface 515 is, for example, an inclined surface, and can match with the inner surface of the headgear secure assembly 520, so as to further press the headgear secure assembly 520 between the transition surface 515 and the interference structure 513.

The first ring portion 511 has a channel 516 extended on a surface of an outer periphery thereof. The channel 516 may be used for fitting with a stop portion 1014 on the ring structure 1011 of the cushion assembly 10. Thus, the first ring portion 511 and the cushion assembly 10 may be engaged by means of snap-fit connection in between. As shown in FIG. 27, the stop portion 1014 may be, for example, a ridge close to the first end of the cushion assembly 10. When the connecting ring structure 510' is engaged with the cushion assembly 10, the stop portion 1014 may be correspondingly positioned in the channel 516 of the first ring portion 511. The ridge is rotatable and mobile along a path of the channel in the channel 516, such that the cushion assembly 10 is rotatable relative to the connecting ring structure 510' to a certain extent after the cushion assembly 10 is engaged with the connecting ring structure 510'.

In one implementation aspect, an outer diameter of the first ring portion 511 gradually decreases from an intersection between the first ring portion 511 and the second ring portion 512 in a direction towards the cushion assembly 10, such that a wall thickness of the first ring portion 511 decreases in a direction from the middle of the connecting ring structure 510' towards the cushion assembly 10. Accordingly, when the cushion assembly 10 is engaged, the first ring portion 511 provides a small amount of deformation to facilitate the stop portion 1014 on the ring structure 1011 of the cushion assembly 10 to reach the channel 516 on the first ring portion 511.

The elbow assembly 40 and the headgear secure assembly 520 are respectively attached to inner and outer sides of the connecting ring structure 510'. In other words, the second ring portion 512 in use is configured between the headgear secure assembly 520 and the elbow assembly 40. After the assembly, the elbow assembly 40 and the headgear secure assembly 520 are not physically in contact in between.

The second ring portion 512 may additionally have an inner flange 517 axially projecting inwards on an inner side thereof. With respect to the engaging of the elbow assembly 40 and the connecting ring structure 510', the inner flange 517 may be accommodated in the ring groove 412 of the elbow assembly 40. Thus, the elbow assembly 40 is rotatably attached to the connecting ring structure 510'. Preferably, the elbow assembly 40 is connected in a non-detach-able manner to the connecting ring structure 510'.

Due to changes in inner diameters of the first ring portion 511 and the second ring portion 512, a step portion 518 is formed at a boundary between the two. The elbow assembly 40 may have a blocking portion 413 on one end thereof. The blocking portion 413 is for blocking the step portion 518 at the boundary between the first ring portion 511 and the second ring portion 512 to provide a blocking effect, so that the elbow assembly 40 can be more stable during a rotation. The blocking effect prevents the elbow assembly 40 from being removed from the connecting ring structure 510' from an outer side.

10. Functionality of the Cushion Assembly on Air Intake/Exhaust

Figure 29:
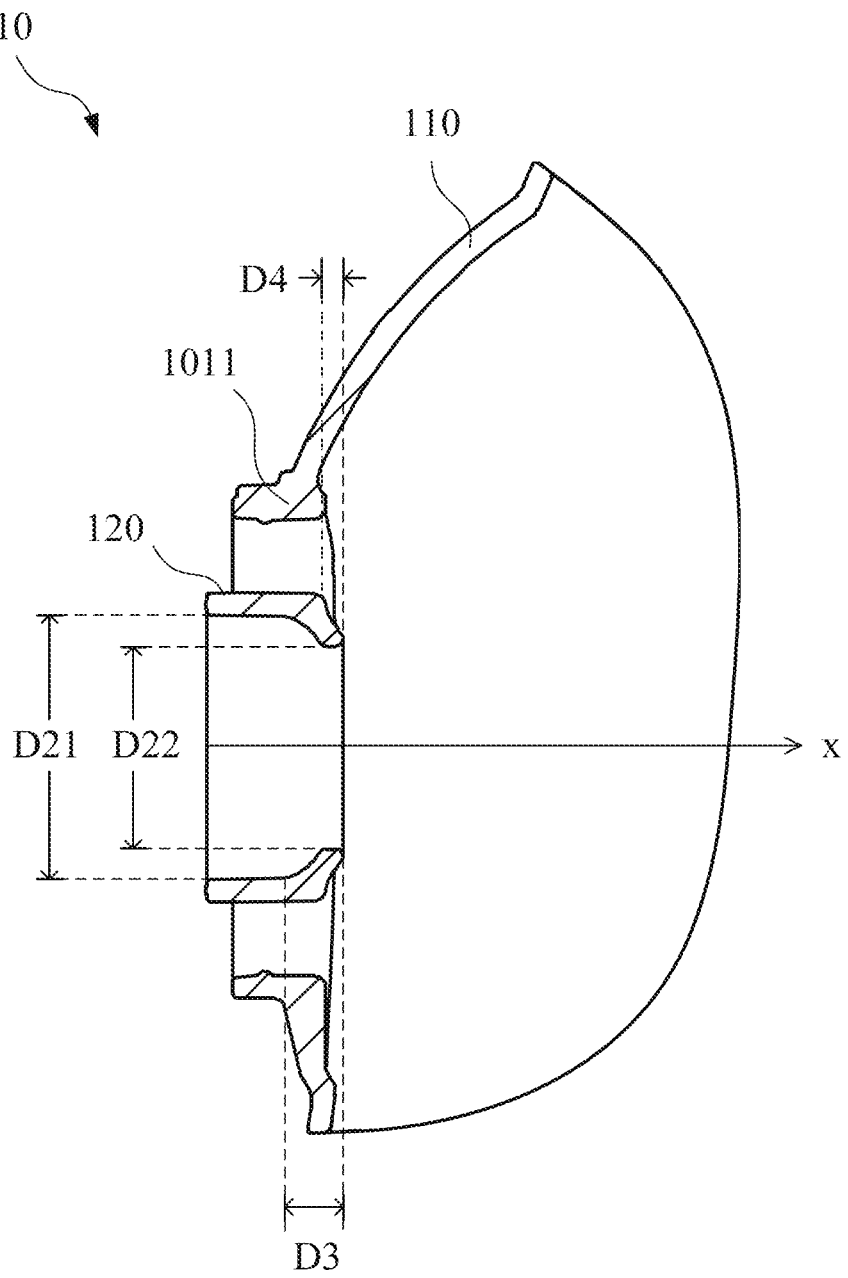
FIG. 29 is a section schematic diagram of a cylindrical wall of a cushion assembly according to an embodiment of the present invention.

Refer to FIG. 29 showing a section schematic diagram of a cylindrical wall of a cushion assembly according to an embodiment of the present invention. The structural shape of the cylindrical wall 120 in the cushion assembly 10 provides an air flow flowing through with a guiding effect, further producing a change in an exit direction for the air flow flowing through and exiting the cylindrical wall 120. In particular, the structural shape of the cylindrical wall 120 provides the air flow passing through the elbow assembly 40 and turned and deflected with an excellent guiding effect, as shown in FIG. 22.

In one implementation aspect, for the cylindrical wall 120 in the cushion assembly 10, the diameter of the cylindrical wall 120 is reduced towards one end of the cushion assembly 10 according to a reduction rate. Taking the inner diameter of the cylindrical wall 120 in FIG. 29 for example, the inner diameter of the cylindrical wall 120 before the change is the initial diameter D21, the inner diameter of the cylindrical wall 120 after the change is the reduced diameter D22, and a change segment D3 refers to a length of the cylindrical wall 120 with a reduction change in an axial direction of the center axis X of the cylindrical wall 120. The reduction rate refers to that, within the length of the change segment D3, the diameter of the cylindrical wall 120 is changed from the initial diameter D21 by 5% to 25% to become the diameter D22, and the length of the change segment D3 does not exceed 10 mm. In a preferred embodiment, the reduction rate reduces the diameter of the cylindrical wall 120 by 7.5% to 22.5% within the change segment D3 having a length of 8 mm. In another preferred embodiment, the reduction rate reduces the diameter of the cylindrical wall 120 by 10% to 20% within the change segment D3 having a length of 6 mm.

In another implementation aspect, a ratio of an opening area of an opening at an air flow inlet end of the cylindrical wall 120 to an opening area of an opening at an air flow outlet end of the cylindrical wall 120 is between 0.5 and 0.95. The opening area of the opening at an air flow inlet end of the cylindrical wall 120 is based on the size of the initial diameter D21, and the opening area of the opening at the air flow outlet end of the cylindrical wall 120 is based on the reduced diameter D22. The cylindrical wall 120 has an extension segment D4 projecting from an end edge of the ring structure 1011 of the cushion assembly 10 in a direction parallel to the center axis X, and a distance of the extension segment D4 is preferably 1 mm to 10 mm. The extension segment D4 substantially extends into the air flow space, breathing chamber or inflating chamber above.

Thus, the cylindrical wall 120 having a guiding effect is capable of alleviating the level of impact imposed by an outgoing air flow upon the mouth and nose of the patient. Moreover, a flow diversion effect is at the same time provided for an incoming air flow field and an outgoing air flow filed, further enabling the air flow exhaled by the patient when in use to smoothly flow to the air flow space, breathing chamber or inflating chamber and further be discharged to the ambient environment via the air pathways (exhaust ducts) 44 shown in FIG. 21 and FIG. 23.

Figure 30:
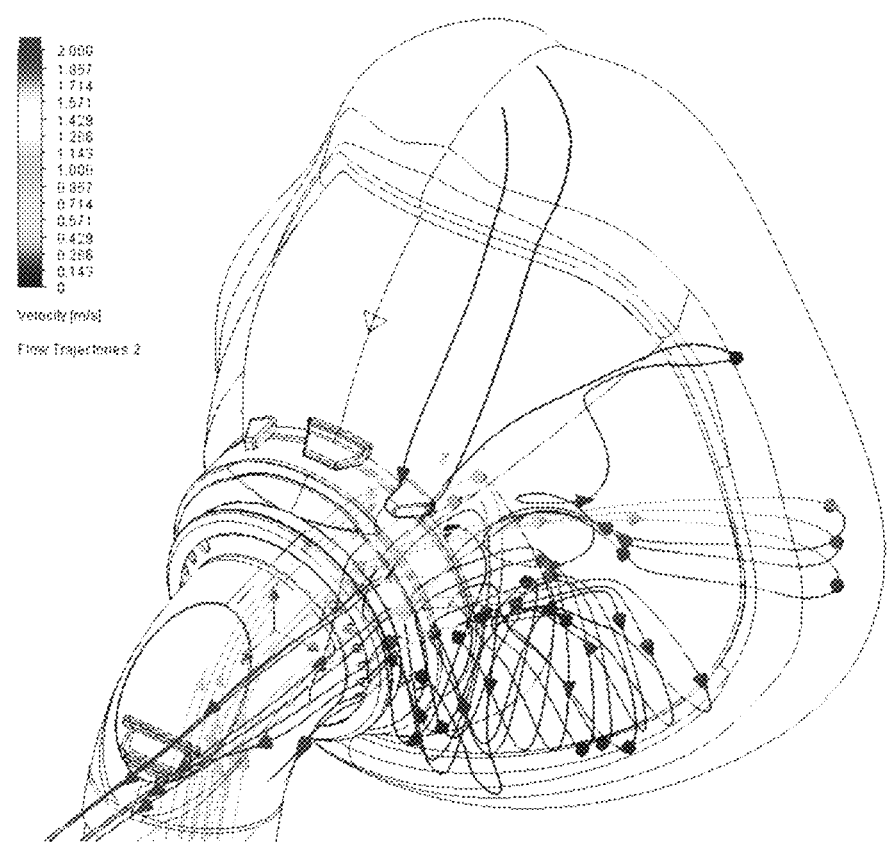
FIG. 30 is an analysis diagram of a flow field disclosed according to an embodiment of the present invention.
Figure 31:
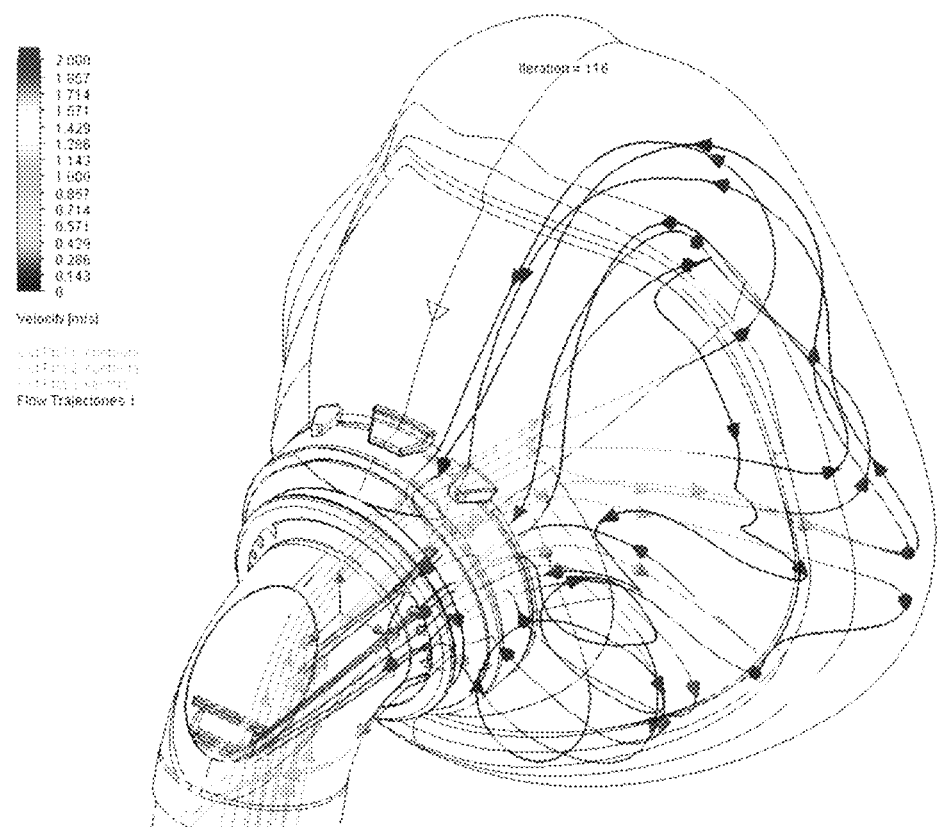
FIG. 31 is an analysis diagram of a flow field disclosed according to another embodiment of the present invention.
Figure 32:
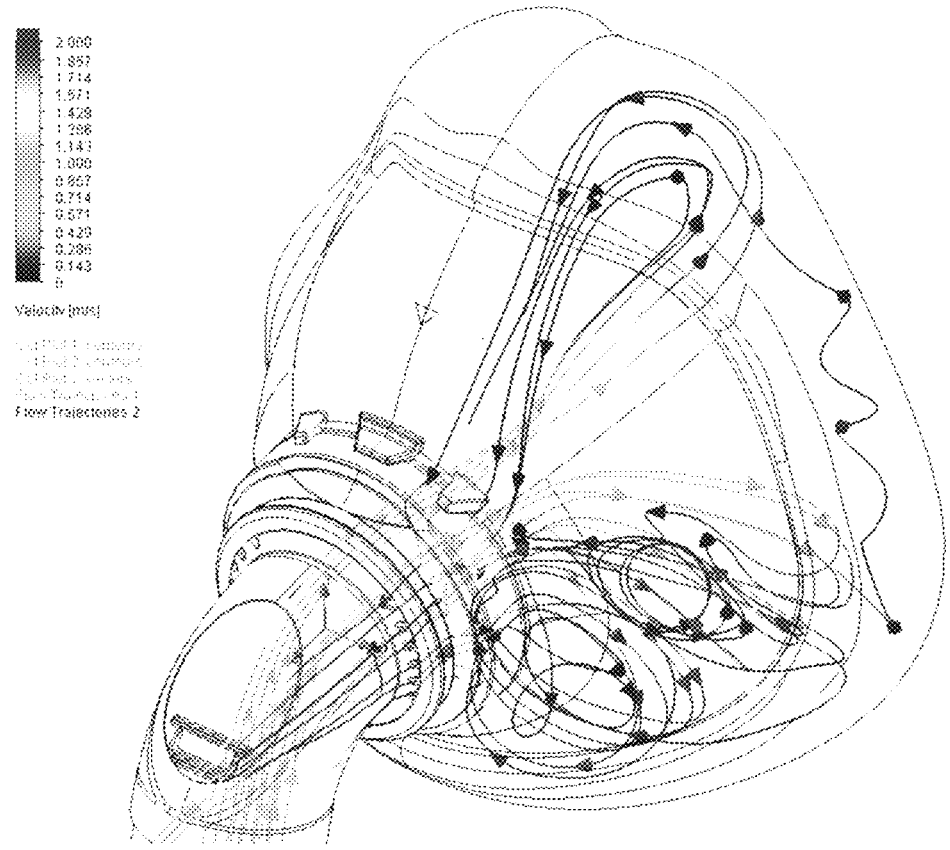
FIG. 32 is an analysis diagram of a flow field disclosed according to yet another embodiment of the present invention.

Referring to FIG. 30, FIG. 31 and FIG. 32, FIG. 30 shows an analysis diagram of a flow field disclosed according to an embodiment of the present invention, FIG. 31 shows an analysis diagram of a flow field disclosed according to another embodiment of the present invention, and FIG. 32 shows an analysis diagram of a flow field disclosed according to yet another embodiment of the present invention.

FIGS. 30 to 32 show flow fields of air flows flowing in the air flow space, breathing chamber or inflating chamber described above. The analysis diagram of the flow field shown in FIG. 30 relates to a situation where an end portion of a cylindrical wall of a patient interface has an eaves portion encircling by 60 degrees (also referring to the eaves portion encircling by 270 degrees shown in FIG. 12). The analysis diagram of the flow field shown in FIG. 31 relates to a situation where an end portion of a cylindrical wall of a patient interface has an eaves portion encircling by 270 degrees. The analysis diagram of the flow field shown in FIG. 32 relates to a situation where an end portion of a cylindrical wall of a patient interface has an eaves portion encircling by 360 degrees.

In FIG. 30, flow field guidance is obviously present along the hollow structure and the inner wall surface of the seal assembly in the breathing chamber. Moreover, obvious guiding air flows flowing to the air pathways (exhaust ducts) are produced at the upper portion of the breathing chamber. In FIG. 31, guiding air flows flowing to the air pathways (exhaust ducts) at the upper portion of the breathing chamber are even more obvious. In FIG. 32, guiding air flows flowing to the air pathways (exhaust ducts) are further reinforced. Therefore, with the patient interface that uses a cushion assembly with a cylindrical wall, a flow diversion effect for an incoming air flow field and an outgoing air flow field is emphasized, and noise is also improved while smooth flow fields are provided.

11. The Position, Securing and Stability of Sealing

The seal forming assembly 140 shown in FIG. 6 is adapted to seal a face of a patient in response to wearing of the patient. Distribution positions of support areas in the seal forming assembly 140 provide further improvement with respect to the wearing comfort of the wearer and the securing stability on the face of the patient. Moreover, the headgear assembly 20 shown in FIG. 16 and FIG. 18 provide excellent multiplied effects in aspects of stably securing the patient interface with comfort on the face of the patient.

The present disclosure is illustrated by various aspects and embodiments. However, persons skilled in the art understand that the various aspects and embodiments are illustrative rather than restrictive of the scope of the present disclosure. After perusing this specification, persons skilled in the art may come up with other aspects and embodiments without departing from the scope of the present disclosure. All equivalent variations and replacements of the aspects and the embodiments must fall within the scope of the present disclosure. Therefore, the scope of the protection of rights of the present disclosure shall be defined by the appended claims.

What is claimed is:

1. A patient interface for continuous positive airway pressure (CPAP) therapy, comprising:

a cushion assembly, comprising:

a shield, having an opening structured on a first end of the cushion assembly and a ring structure;

a cylindrical wall, provided to the opening by a plurality of support structures and configured to be concentric with the opening; and a sealing assembly, provided to the shield of the cushion assembly and together form a breathing chamber, the sealing assembly adapted to seal a face of a patient;

wherein the ring structure projects outwardly from the opening in a direction away from the breathing chamber, the cylindrical wall projects outwardly in the direction away from the breathing chamber with a same inner diameter along its length, the cylindrical wall further projects towards a second end opposite to the first end of the cushion assembly with a gradually decreasing inner diameter along its extending direction, wherein the cylindrical wall projects toward the breathing chamber beyond an end surface to extend into the breathing chamber, the end surface being defined by an end edge of the opening that faces and at which the opening opens into the breathing chamber;

a headgear assembly, including a plurality of straps for fixing the patient interface in use;

an elbow assembly, adapted to be in fluid communication with the cushion assembly to deliver an air flow to airways of the patient when in use;

a connecting ring structure, having one end connected to the cushion assembly and one other end non-detachably connected to the elbow assembly; and a headgear secure assembly, adapted to engage with the connecting ring structure, the headgear secure assembly including a plurality of slots adapted to attach to the corresponding straps in use, wherein the headgear secure assembly is not provided with a forehead support, wherein the connecting ring structure has a first limiting portion, the first limiting portion is structured to correspond and interfere a second limiting portion on the headgear secure assembly when in use, a width of the first limiting portion is slightly greater than a width of the second limiting portion to provide a rotation angle between the headgear secure assembly and the cushion assembly, wherein the cushion assembly, the elbow assembly, and the headgear secure assembly are assembled together via the connecting ring structure.

2. The patient interface according to claim 1, wherein the cylindrical wall projects in the manner of having a same inner diameter in the direction away from the breathing chamber by a first distance, the cylindrical wall projects in the manner of having a decreasing inner diameter towards the second end opposite to the first end of the cushion assembly by a second distance, and the first distance is greater than the second distance.

3. The patient interface according to claim 2, wherein the cylindrical wall projects in the manner of having the gradually decreasing inner diameter towards the second end of the cushion assembly to form a head having a truncated hollow conical shape.

4. The patient interface according to claim 1, wherein the connecting ring structure and the cushion assembly are rotatable in between when attached.

5. The patient interface according to claim 1, wherein the shield and the sealing assembly are integral-molded.

6. The patient interface according to claim 1, wherein the cushion assembly, the elbow assembly and the headgear secure assembly excludes direct physical contact or physical engaging when in use.

7. The patient interface according to claim 1, wherein the support structures are configured to be of a stalk form, each of the support structures has one end connected to an outer surface of the cylindrical wall and one other end connected to an inner surface of the opening of the shield, and the support structures are in an asymmetric arrangement relative to an axis of the cylindrical wall.

8. The patient interface according to claim 7, wherein the elbow assembly comprises a plurality of concavities provided on an outer surface of a first end of the elbow assembly, the plurality of concavities and an inner surface of the connecting ring structure together form a plurality of exhaust ducts when the first end of the elbow assembly is engaged with the connecting ring structure, the exhaust ducts are for an outgoing air flow from the breathing chamber to an ambient environment to pass through, the support structures are in flow communication with the exhaust ducts, and two adjacent of the support structures having a shortest distance in between along an outer surface of the cylindrical wall configured to correspond to a nose of an patient wearing the patient interface.

9. The patient interface according to claim 8, wherein the elbow assembly comprises a body, the body defines, by a bent inner wall, a conduit air pathway that causes most of a delivered air flow to be gathered on an upper portion, a portion of the cylindrical wall projecting towards the second end opposite to the first end of the cushion assembly changes a direction of an outgoing air flow for the air flow delivered from the elbow assembly, such that a main air flow mostly gathered on the upper portion of the conduit air pathway exits the cylindrical wall in an outgoing direction that is non-parallel to an axis of the cylindrical wall, thereby alleviating a degree of impact imposed by the air flow on a mouth and the nose of the patient, and an air flow exhaled by the patient when in use is enabled to smoothly flow to an upper portion of the breathing chamber and be further discharged via the exhaust ducts to the ambient environment.

10. The patient interface according to claim 1, wherein an inner diameter of the cylindrical wall decreases towards the second end opposite to the first end of the cushion assembly by a reduction rate, and the reduction rate reduces the inner diameter of the cylindrical wall within a length of 5 mm to 10 mm by 5% to 25%.

11. The patient interface according to claim 1, wherein a ratio of an opening area of an opening of the cylindrical wall facing the first end of the cushion assembly to an opening area of an opening of the cylindrical wall facing the second end opposite to the first end of the cushion assembly is 0.5 to 0.95, and a length by which a portion of the cylindrical wall projecting toward the second end of the cushion assembly extends into the breathing chamber in a direction parallel to an axis of the cylindrical wall is greater than 1 mm.

12. The patient interface according to claim 1, wherein the connecting ring structure comprises a first ring portion and a second ring portion, an inner diameter of the first ring portion is greater than an inner diameter of the second ring portion, the first ring portion and the cushion assembly are engaged with each other by means of a snap-and-fit connection, the second ring portion is structured to be configured between the headgear secure assembly and the elbow assembly when in use, and the connecting ring structure causes the cushion assembly and the elbow assembly to not be in direct physical contact or physical engagement when in use.

13. The patient interface according to claim 12, wherein the first ring portion comprises an extending channel, the channel is for a stop portion on the ring structure of the cushion assembly to perform fastening, the second ring portion has at an end edge thereof an interference structure projecting radially outwards, the interference structure causes the connecting ring structure to be fastened at a central aperture of the headgear secure assembly, the second ring portion has at an inner side thereof an inner flange radially projecting inwards, the inner flange is structured to be accommodated in a ring groove on the elbow assembly when in use, the elbow assembly has on one end thereof a blocking portion, the blocking portion is structured to stop at a boundary between the first ring portion and the second ring portion, and an outer diameter of the first ring portion gradually decreases from the boundary of the first ring portion and the second ring portion in a direction towards the second end of the cushion assembly.

14. The patient interface according to claim 1, wherein the seal forming assembly comprises a first support area provided at the shield and a second support area extended from the first support area, a border is formed between the first support area and the second support area, a position where the seal forming assembly extends from a boundary between the shield and the first support area and the thickness gradually decreases to a predetermined thickness is defined as the border, and the predetermined thickness is any value selected from a range between 0.50 mm and 0.70 mm.

15. The patient interface according to claim 1, wherein the seal forming assembly comprises a first support area provided at the shield and a second support area extended from the first support area, a first border is formed between the shield and the first support area, a second border is formed between the first support area and the second support area, a position where the seal forming assembly extends from the first border and the thickness gradually decreases to a predetermined thickness is defined as the second border, between a position of each point on the first border and the second border has a vertical distance, and among the vertical distances, the corresponding vertical distances adjacent to cheeks and cheekbones of the patient when in use are greater than the corresponding vertical distances adjacent to a nose and a chin of the patient when in use.

16. The patient interface according to claim 1, wherein the headgear assembly comprises two upper straps and a plurality of lower straps for position adjustment, and comprises a rear portion configured to reach at least a part of an occipital bone of an patient when in use, the rear portion comprises a top portion, two side portions and a bottom portion, the top portion is provided between the side portions, the bottom portion is provided between the side portions and the lower straps, the plurality of upper straps are provided to the corresponding side portions, between each of the side portions and the top portion is a first engaging line, between each of the upper straps and the corresponding side portion is a second engaging line, between each of the side portions and the bottom portion is a third engaging line, a distance between centers of two of the first engaging lines is a first strap distance, a distance between centers of two of the second engaging lines is a second strap distance, a distance between centers of two of the third engaging lines is a third strap distance, and the first strap distance is smaller than the second strap distance but greater than the third strap distance.

\* \* \* \* \*